US010859457B2

(12) United States Patent
Leuschner et al.

(10) Patent No.: US 10,859,457 B2
(45) Date of Patent: Dec. 8, 2020

(54) SENSOR DEVICE INCLUDING SENSOR UNIT FOR A GASEOUS MEDIUM

(71) Applicant: Infineon Technologies AG, Neubiberg (DE)

(72) Inventors: Rainer Leuschner, Regensburg (FR);
Kerstin Kaemmer, Radebeul (DE);
Roland Meier, Regensburg (DE);
Marten Oldsen, Anzing (DE);
Karolina Zogal, Regensburg (DE)

(73) Assignee: INFINEON TECHNOLOGIES AG, Neubiberg (DE)

( * ) Notice: Subject to any disclaimer, the term of this patent is extended or adjusted under 35 U.S.C. 154(b) by 465 days.

(21) Appl. No.: 15/808,044

(22) Filed: Nov. 9, 2017

(65) Prior Publication Data

US 2018/0136064 A1    May 17, 2018

(30) Foreign Application Priority Data

Nov. 11, 2016   (DE) ........................ 10 2016 121 683

(51) Int. Cl.
*G01L 9/00*     (2006.01)
*G01N 33/00*    (2006.01)
(52) U.S. Cl.
CPC .......... *G01L 9/0073* (2013.01); *G01L 9/0042* (2013.01); *G01N 33/0027* (2013.01)

(58) Field of Classification Search
CPC .. G01L 9/0073; G01L 9/0042; G01N 33/0027
See application file for complete search history.

(56) References Cited

U.S. PATENT DOCUMENTS

| 2011/0180924 | A1 | 7/2011 | Tian et al. |
| 2012/0177229 | A1 | 7/2012 | Lorenz et al. |
| 2012/0243721 | A1 | 9/2012 | Inoda et al. |
| 2017/0070337 | A1 | 3/2017 | Giriyappa et al. |
| 2017/0203958 | A1* | 7/2017 | Classen ................ B81B 7/0048 |

FOREIGN PATENT DOCUMENTS

| DE | 10353767 A1 | 6/2005 |
| DE | 102016106263 A1 | 10/2016 |

* cited by examiner

*Primary Examiner* — Dennis White
(74) *Attorney, Agent, or Firm* — Slater Matsil, LLP

(57) ABSTRACT

A sensor device includes a sensor unit sensitive for a property of a gaseous medium. The sensor unit is formed on a first surface of a sensor substrate. A frame structure on the first surface includes a first loop portion laterally surrounding a first area that includes the sensor unit. A communicating channel accesses the first area through at least one of a lateral port in the first loop portion and a base port in the sensor substrate. A lid structure completely covers the frame structure and the first area.

24 Claims, 31 Drawing Sheets

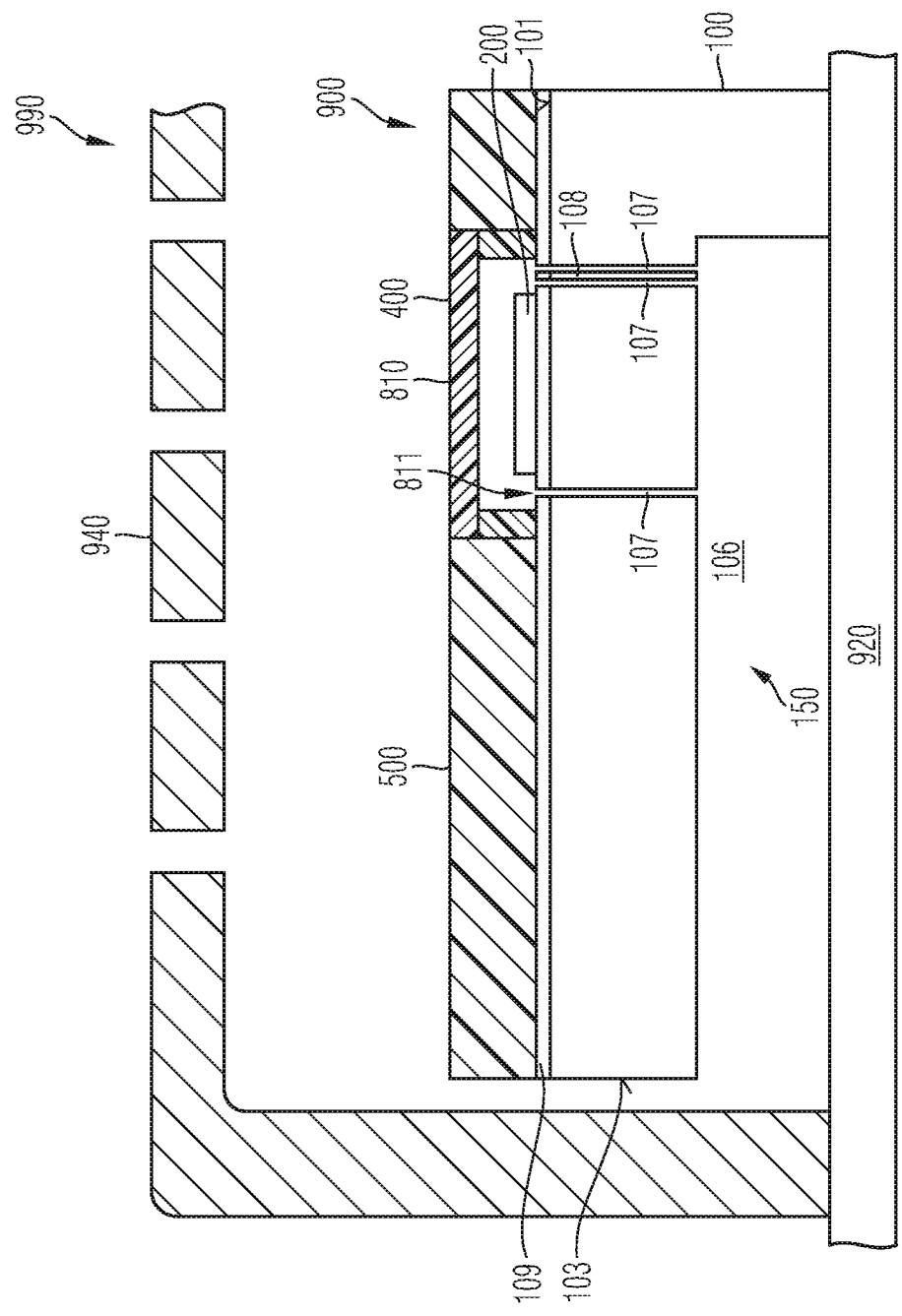

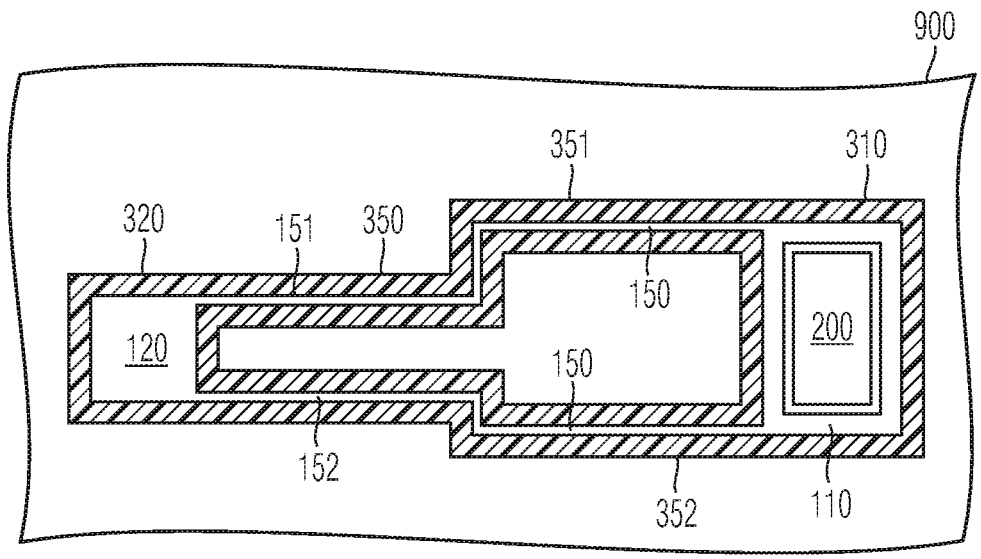
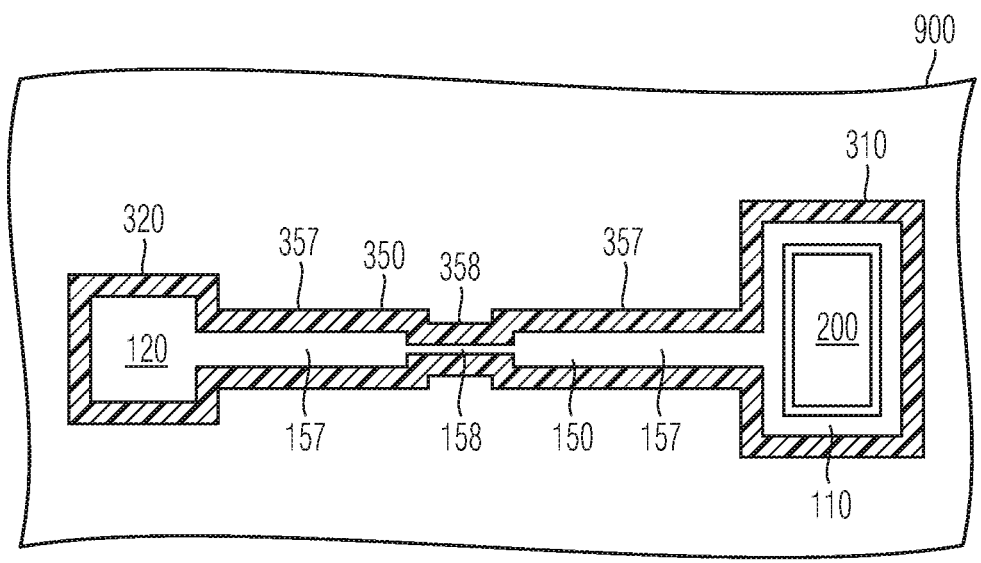

SENSOR DEVICE INCLUDING SENSOR UNIT FOR A GASEOUS MEDIUM

This application claims the benefit of Germany Application No. 102016121683.6, filed on Nov. 11, 2016, which application is hereby incorporated herein by reference in its entirety.

BACKGROUND

Integrated sensor devices integrate a sensor unit, which is sensitive to a physical or chemical property of a probe, with electronic circuits for controlling the sensor unit and for interfacing the sensor unit to an electronic circuit or to a user. Some types of integrated sensor devices such as pressure sensors and gas sensors are exposed to a gaseous medium, for example, the atmosphere in a process chamber or ambient atmosphere and include sensitive surfaces, for example surfaces with selective receptors for chemical compounds or deflectable membranes.

There is a need for increasing reliability of integrated sensor devices.

SUMMARY

The present disclosure relates to a sensor device including a sensor unit that is sensitive for a property of a gaseous medium. The sensor unit is on a first surface of a sensor substrate. A frame structure on the first surface includes a first loop portion laterally surrounding a first area that includes the sensor unit. A communicating channel accesses the first area through at least one of a lateral port in the first loop portion and a base port in the sensor substrate. A lid structure completely covers the frame structure and the first area.

The present disclosure further relates to a method of manufacturing a sensor device that includes forming a sensor unit sensitive for a property of a gaseous medium on a front surface of a semiconductor substrate. A frame structure is formed on the front surface, wherein the frame structure includes a first loop portion laterally surrounding a first area that includes the sensor unit, a second loop portion laterally surrounding a second area, and a connection portion connecting the first loop portion with the second loop portion to form a communicating channel between the first and second areas. A lid structure is formed on the frame structure. A lid opening selectively exposing the second area is formed in the lid structure.

The present disclosure also relates to a sensor device including a sensor box encasing a first area that includes a sensor unit sensitive for a property of a gaseous medium, wherein the sensor unit is formed on a first surface of a sensor substrate. An inlet box adjacent to the sensor box partially encases a second area and includes a lid opening opposite to the first surface. A conduit includes a communicating channel that extends from a lateral port that opens into the first area to a lateral port that opens into the second area.

In addition, the present disclosure relates to a sensor device including a sensor unit that is sensitive for a property of a gaseous medium. The sensor unit is on a first surface of a sensor substrate. A frame structure on the first surface includes a first loop portion laterally surrounding a first area that includes the sensor unit. A second loop portion surrounds a second area. A connection portion connects the first loop portion with the second loop portion to form a communicating channel between the first and second areas. A lid structure on the frame structure includes a lid opening that selectively exposes the second area.

Further embodiments are defined in the dependent claims. Those skilled in the art will recognize additional features and advantages upon reading the following detailed description and on viewing the accompanying drawings.

BRIEF DESCRIPTION OF THE DRAWINGS

The accompanying drawings are included to provide a further understanding of the invention and are incorporated in and constitute a part of this specification. The drawings illustrate the embodiments of the present invention and together with the description serve to explain principles of the invention. Other embodiments of the invention and intended advantages will be readily appreciated as they become better understood by reference to the following detailed description.

FIG. 2F is a schematic vertical cross-sectional view of a portion of a sensor device including the sensor device of FIG. 2E and a carrier substrate;

FIG. 8C is a schematic horizontal cross-sectional view of a portion of an integrated sensor device in the plane of the frame structure according to an embodiment with a communicating channel including two parallel tubes;

FIG. 8D is a schematic horizontal cross-sectional view of a portion of an integrated sensor device in the plane of the frame structure according to an embodiment concerning a communicating channel with narrow section;

DETAILED DESCRIPTION OF ILLUSTRATIVE EMBODIMENTS

In the following detailed description, reference is made to the accompanying drawings, which form a part hereof and in which are shown by way of illustrations specific embodiments in which the invention may be practiced. It is to be understood that other embodiments may be utilized and structural or logical changes may be made without departing from the scope of the present invention. For example, features illustrated or described for one embodiment can be used on or in conjunction with other embodiments to yield yet a further embodiment. It is intended that the present invention includes such modifications and variations. The examples are described using specific language, which should not be construed as limiting the scope of the appending claims. The drawings are not scaled and are for illustrative purposes only. Corresponding elements are designated by the same reference signs in the different drawings if not stated otherwise.

The terms "having", "containing", "including", "comprising" and the like are open, and the terms indicate the presence of stated structures, elements or features but do not preclude additional elements or features. The articles "a", "an" and "the" are intended to include the plural as well as the singular, unless the context clearly indicates otherwise.

Figure 1A:
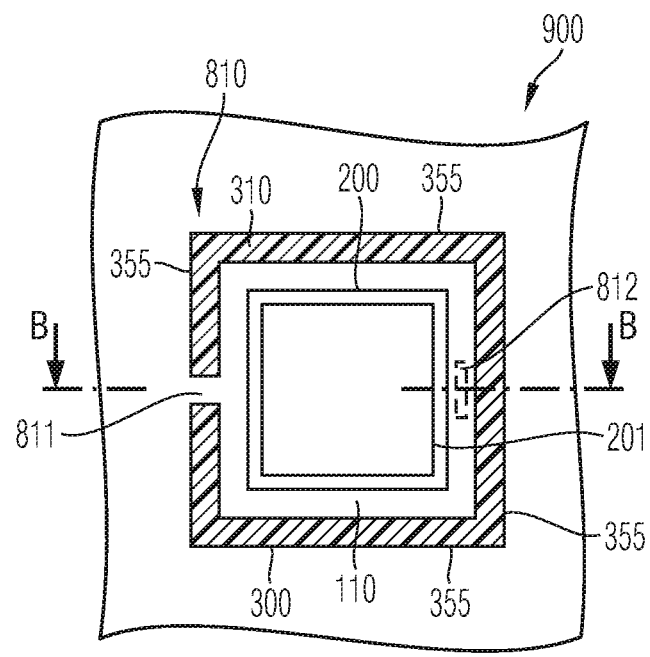
FIG. 1A is a schematic horizontal cross-sectional view of a portion of an integrated sensor device with a frame structure surrounding a sensor area and a communicating channel accessing the sensor area through at least one of a lateral port and a base port according to an embodiment.
Figure 1B:
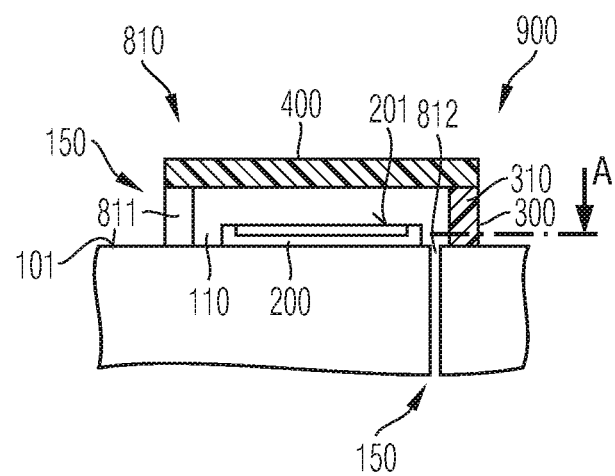
FIG. 1B is a schematic vertical cross-sectional view of the sensor device portion of FIG. 1A along line B-B.

FIGS. 1A to 1B illustrate a sensor box 810 formed on a first surface 101 of a sensor substrate 100, wherein the sensor box 810 encases a sensor unit 200.

The sensor unit 200 may be any kind of sensor exposed to a gaseous medium and capable of determining a physical characteristic of the gaseous medium or suitable for determining any constituent of the gaseous medium, wherein to this purpose a sensitive surface of the sensor unit 200 is exposed to the gaseous medium. The gaseous medium may be the atmosphere in a closed chamber or ambient atmosphere, by way of example.

For example, the sensor unit 200 may be an MEMS (micro-electromechanical system), e.g., an MEMS pressure sensor, wherein the sensitive surface 201 is a deflectable membrane spanning across a hermetically closed cavity in the sensor unit 200, wherein a degree of deflection is related to the ambient pressure and deflection of the membrane detunes a measurement capacity. According to another embodiment the sensor unit 200 is a gas sensor with a sensitive surface 201 including selective receptor sites for the molecules of interest.

The sensor substrate 100 at least includes electrically conductive connection lines connecting electrical terminals of the sensor unit 200 with contact pads accessible, e.g., for wire bonds. An interlayer dielectric separates the connection lines from each other and from further conductive structures in the sensor substrate 100. The sensor substrate 100 may include a semiconductor portion including integrated circuits for interfacing the sensor unit 200 to other electronic devices, for supplying portions of the sensor unit 200 with a supply voltage and/or measurement amplifiers and impedance converters. For example, the semiconductor portion may include a read-out circuit for interfacing a capacitance change induced by deflection of a deflectable membrane of a pressure sensor into an electric signal output to other electronic circuits.

The sensor unit 200 may be directly on a topmost passivation layer that covers connection lines between the sensor unit 200, electronic circuits in the sensor substrate 100, and contact pads on the first surface 101.

A normal to the first surface 101 defines a vertical direction. Directions parallel to the first surface 101 are horizontal directions.

Directly on the first surface 101 a frame structure 300 forms a closed frame with a first loop portion 310 surrounding a first area 110 on the first surface 101. The first area 110 forms a sensor area including the sensor unit 200. The frame structure 300 may include straight line sections 355 that may have uniform width as illustrated in FIG. 1A, wherein a horizontal cross-section of the first area 110 may be a polygon, e.g., a rectangle. According to other embodiments, the width of line sections of the frame structure 300 may vary or the frame structure 300 may cover more or all portions of the first surface 101 outside of the first area 110.

A lid structure 400 covers the frame structure 300. The lid structure 400 completely covers the first area 110 with the sensor unit 200 such that the first loop portion 310 of the frame structure 300 and the lid structure 400 form a sensor box 810 with only one or more lateral ports 811 or a base port 812 opening into the communicating channel 150 that may include several parallel tubes. The lid structure 400 is vertically spaced from the sensitive surface 201 of the sensor unit 200. A vertical extension v1 of the frame structure 300 is in a range from 10 µm to 150 µm, for example in a range from 20 µM to 100 µm. A vertical extension v2 of the lid structure 400 may be in a range from 20 µM to 150 µM, for example in a range from 30 µm to 100 µm.

A communicating channel 150 forms or is part of a connection of the first area 110 with the ambient and accesses the first area 110 through at least one of a lateral port 811 in the frame structure 300 or a base port 812 formed in the sensor substrate 100. Since the vertical extensions v1, v2 of the frame structure 300 and the lid structure 400 are comparatively small, a total mounting height of the sensor device 900 is comparatively shallow. Compared to a gas flow to the sensor unit 200 through a mechanical shield or grid mounted above the sensor unit 200, for example, by a wafer bonding process or by a customized packaging process, the access to the sensor area either through the lateral port 811 or through the base port 812 results in only moderate increase of device height and in only moderate increase of process complexity, because the frame structure 300 and the lid structure 400 can be formed by low-cost wafer-level processes.

Figure 2A:
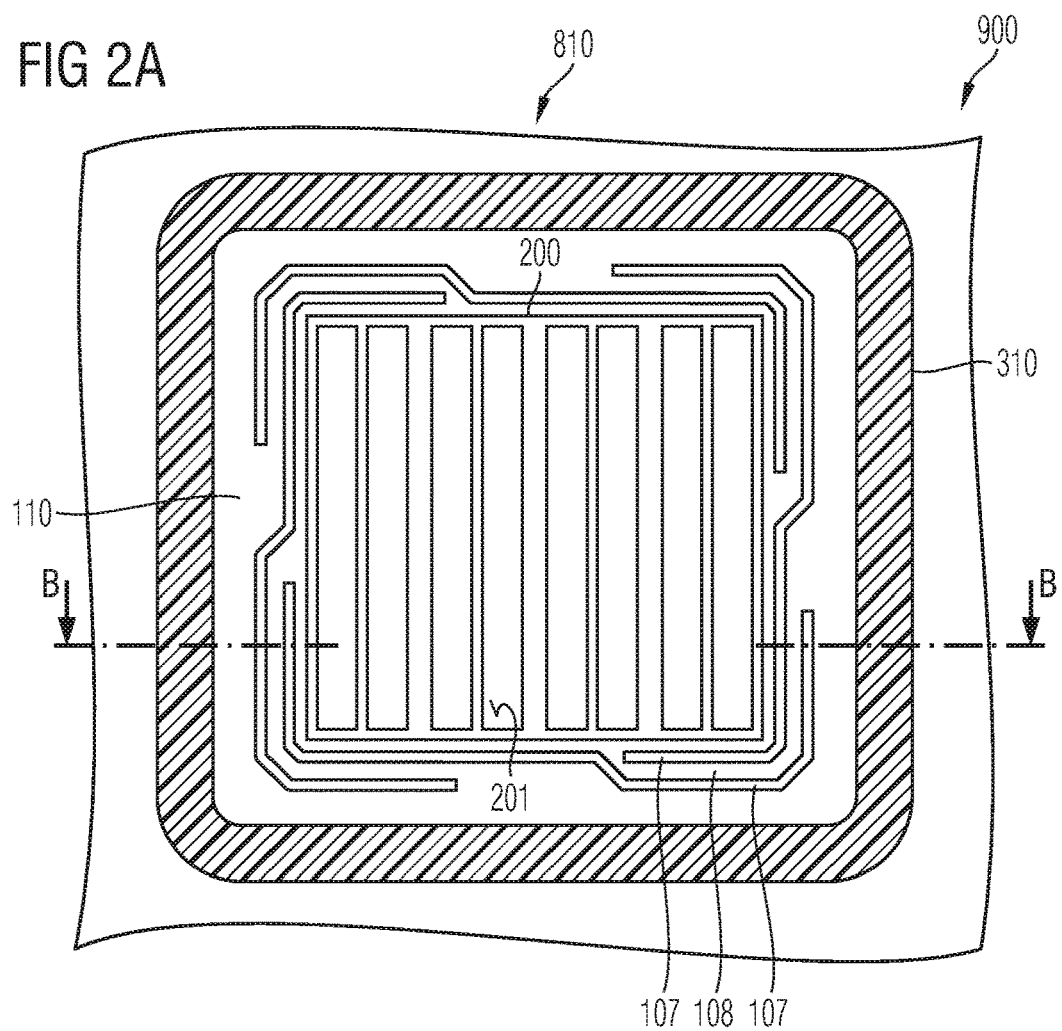
FIG. 2A is a schematic plan view of a portion of an integrated sensor device according to an embodiment with a spring groove forming a base port for a communicating channel and a laterally closed rear side cavity.
Figure 2B:
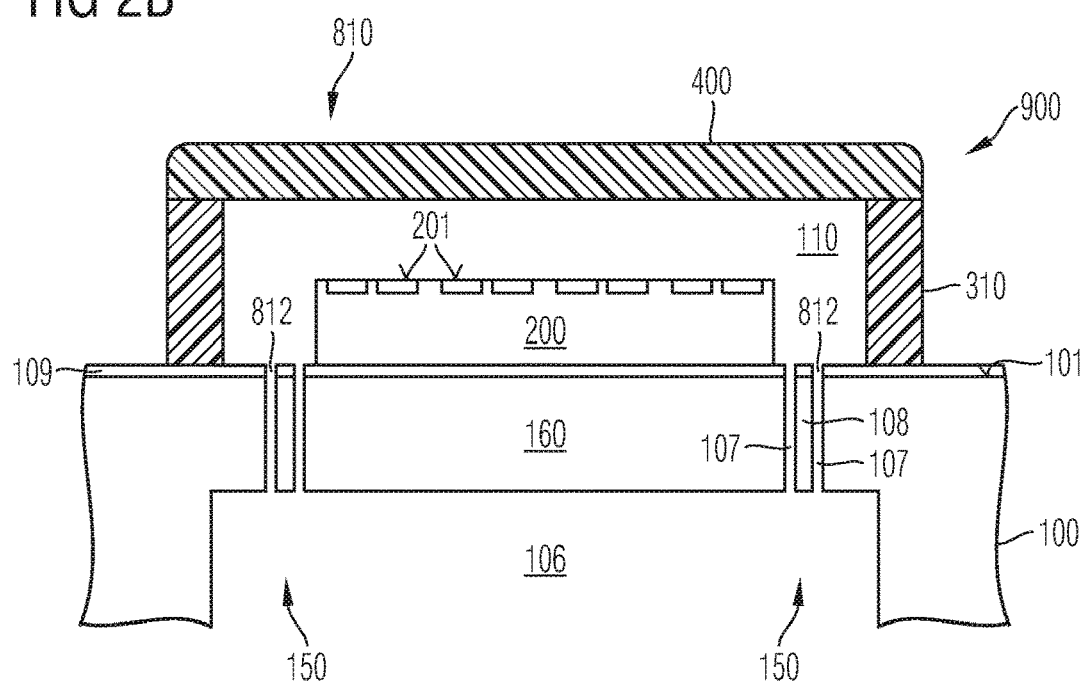
FIG. 2B is a schematic vertical cross-sectional view of the sensor device portion of FIG. 2A along line B-B.
Figure 2C:
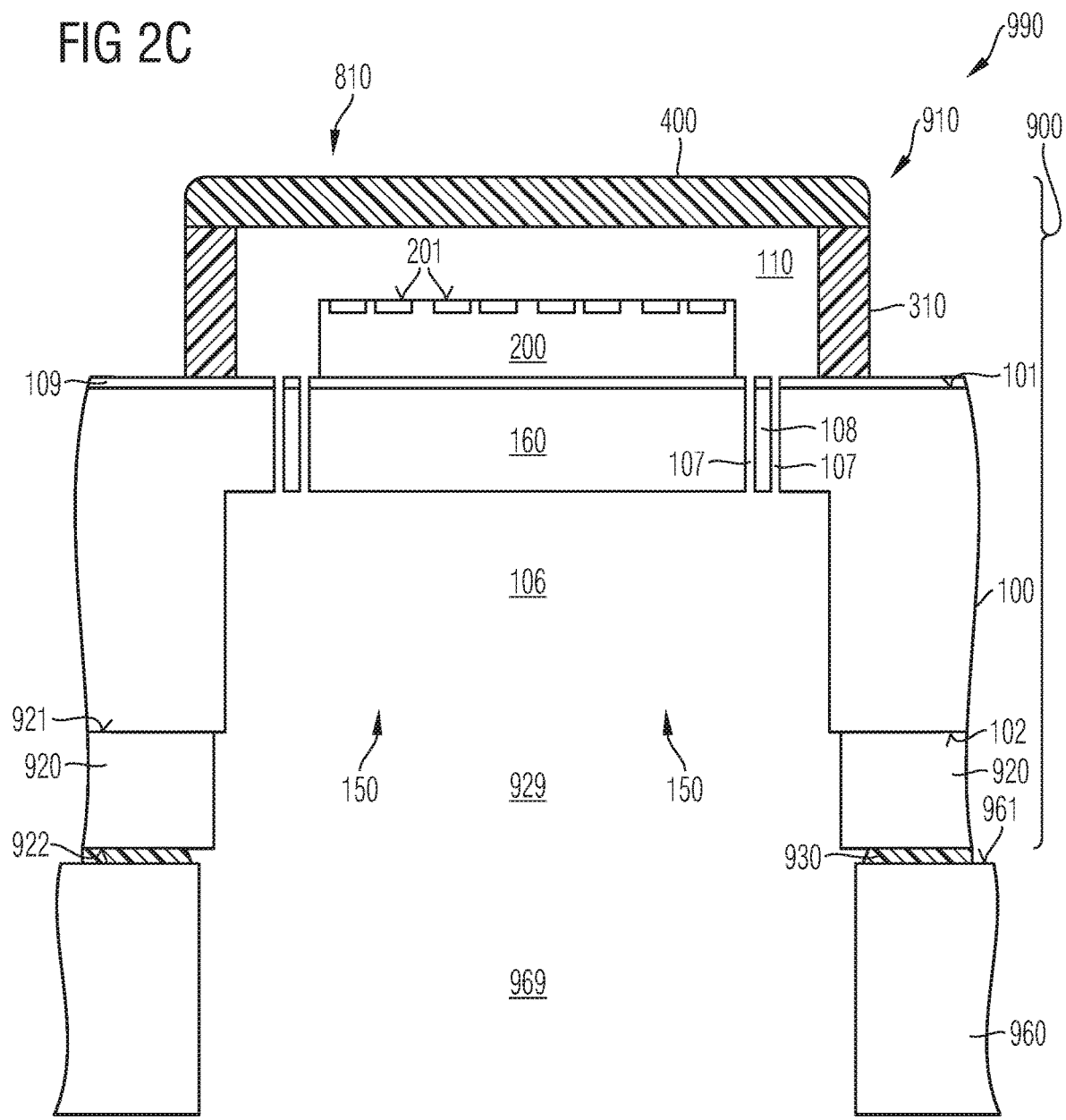
FIG. 2C is a schematic vertical cross-sectional view of a portion of a sensor arrangement including the sensor device of FIGS. 2A to 2B.
Figure 2D:
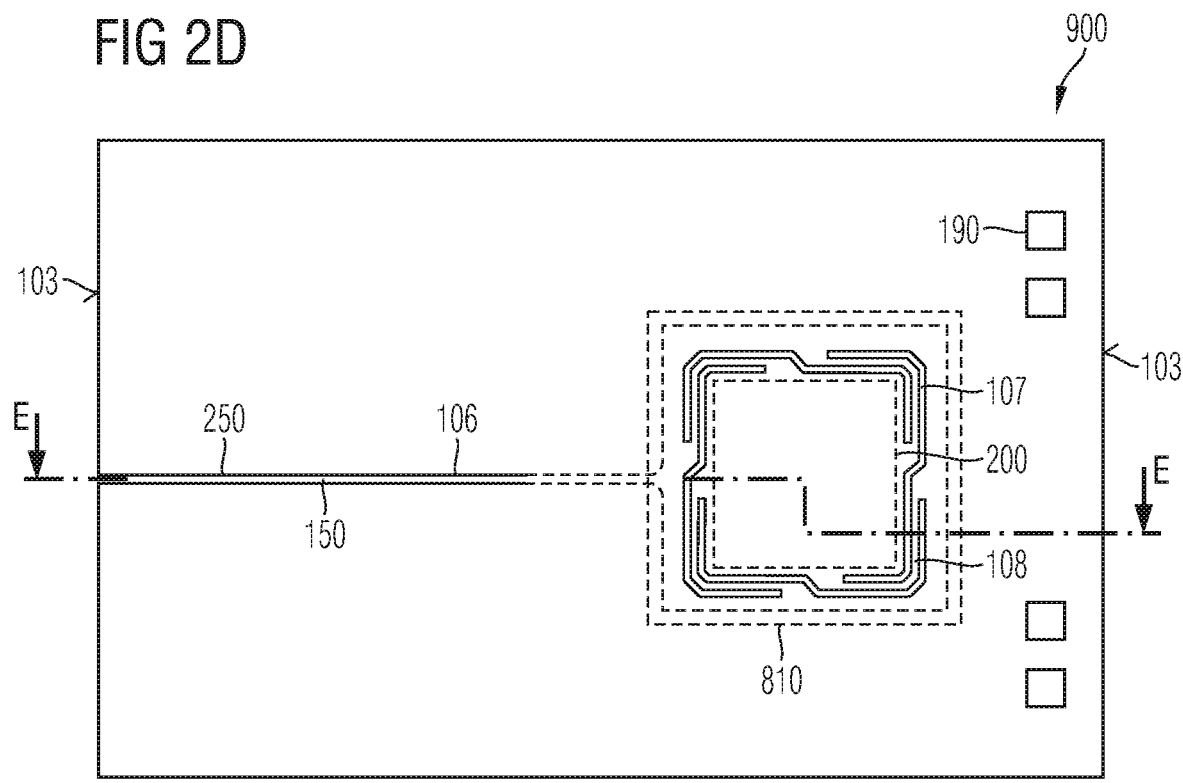
FIG. 2D is a schematic plan view of a portion of an integrated sensor device according to an embodiment with a spring groove forming a base port for a communicating channel and a rear side cavity directly adjoining a lateral outer surface of a sensor substrate.
Figure 2E:
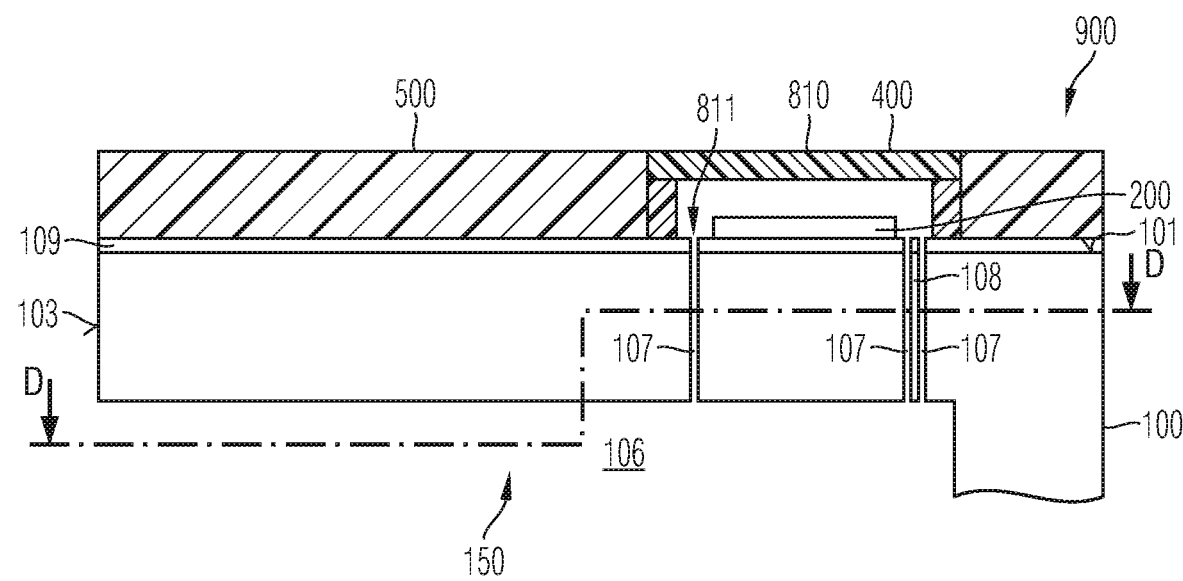
FIG. 2E is a schematic vertical cross-sectional view of the sensor device portion of FIG. 2D along line E-E.

FIGS. 2A to 2F refer to an access to the sensor box 810 through the sensor substrate 100, wherein the sensor device 900 illustrated in FIGS. 2A to 2C includes an access to the sensor box 810 from the back of a sensor substrate 100 and the sensor device 900 illustrated in FIGS. 2D to 2F includes an access to the sensor box 810 through an outer lateral surface 103 of the sensor substrate 100. The approaches can be combined with mounting the sensor unit 200 on a suspended mass 160 mechanically connected to the sensor substrate 100 through spring bars 108.

FIGS. 2A and 2B show a rear side cavity 106 extending from a second surface 102, which is opposite to the first surface 101, into the sensor substrate 100. The rear side cavity 106 is closed in the lateral directions. In addition, narrow, stripe-shaped spring grooves 107 extend from the first surface 101 to the rear side cavity 106. Two neighboring spring grooves 107 running approximately parallel to each other in sections define a spring bar 108 between them, wherein one end of the spring bar 108 is connected to the suspended mass 160 and the opposite end is connected to the sensor substrate 100.

As illustrated in FIG. 2A, spring bars 108 on each side of the suspended mass 160 decouple the sensor unit 200, which is firmly attached to a surface of the suspended mass 160, mechanically from the sensor substrate 100.

The communicating channel 150 includes the rear side cavity 106 and the spring grooves 107 and pipes gas or air from the ambient into the sensor box 810.

A width of the spring grooves 107 may be in a range from 3 μm to 30 μm, for example, in a range from 5 μm to 15 μm. A vertical extension of the spring grooves 107 between the rear side cavity 106 and the first surface 101 may be in a range from 10 μm to 200 μM, for example, from 50 μm to 150 μm. The narrow spring grooves 107 protect the sensor unit 200 against critical particles. Compared to sensor particle protection including a mechanical shield or grid mounted above the sensor unit 200, the sensor device 900 gets along without significant increase of the overall device height.

FIG. 2C shows a sensor arrangement 990 including the sensor device 900 of FIGS. 2A and 2B. The sensor device 900 includes a die portion 910 including the sensor substrate 100 as well as the sensor box 810. The die portion 910 may be mounted on a carrier structure 920, which may include one or more leads wire bonded to contact pads formed on the first surface 101. A first surface 921 of the carrier structure 920 is attached to the second surface 102 of the sensor substrate 100. The carrier structure 920 includes an opening 929 that extends through the carrier structure 920 and that exposes the rear side cavity 106. The opening 929 in the carrier structure 920 connects the communicating channel 150 with the ambient.

For example, as illustrated in the sensor arrangement 990 of FIG. 2C, the sensor device 900 can be mounted on a circuit board 960, wherein a circuit board opening 969 exposes the rear side cavity 106 of the sensor device 900. An adhesion or solder layer 930 may mechanically and, optionally, electrically connect a mounting surface 961 of the circuit board 960 with a mounting surface 922 of the carrier structure 920.

In the sensor device 900 of FIGS. 2D to 2F the rear side cavity 106 directly adjoins an outer lateral surface 103 of the sensor substrate 100, wherein the outer lateral surface 103 is tilted, e.g., orthogonal to the first surface 101 and connects the first surface 101 with the second surface. Air or gas accesses the sensor box 810 through a lateral path in the sensor substrate 100.

FIG. 2D shows a horizontal cross-section of a complete sensor device 900 which includes a sensor box 810 and contact pads 190 at a front side.

The sensor device 900 of FIGS. 2D and 2E deviates from that illustrated in FIGS. 2A to 2B in that the rear side cavity 106 includes one or more narrow portions forming a substrate trench 250 extending from a wide portion, which exposes the spring grooves 107, to the outer lateral surface 103 on one or more lateral sides of the sensor substrate 100. The communicating channel 150 includes the spring grooves 107 and the rear side cavity 106 with the substrate trench 250, which vertical extension is the same as for the rear side cavity 106. A width of the substrate trench 250 may correspond to that of the spring grooves 107. The substrate trench 250 may consist of one straight portion as illustrated in FIG. 2D or may include one, two or several bends and branches as described below.

As illustrated in FIG. 2F, a sensor arrangement 990 may include the sensor device 900 mounted on a carrier structure 920 that covers the rear side cavity 106 as well as the substrate trench 250 on the rear side of the sensor device 900. Gas may flow through an opening in the carrier structure 920 outside of a vertical projection of the sensor substrate 100 or through openings in a metal cap 940 mounted on the carrier structure 920 and enclosing the sensor device 900.

Figure 3A:
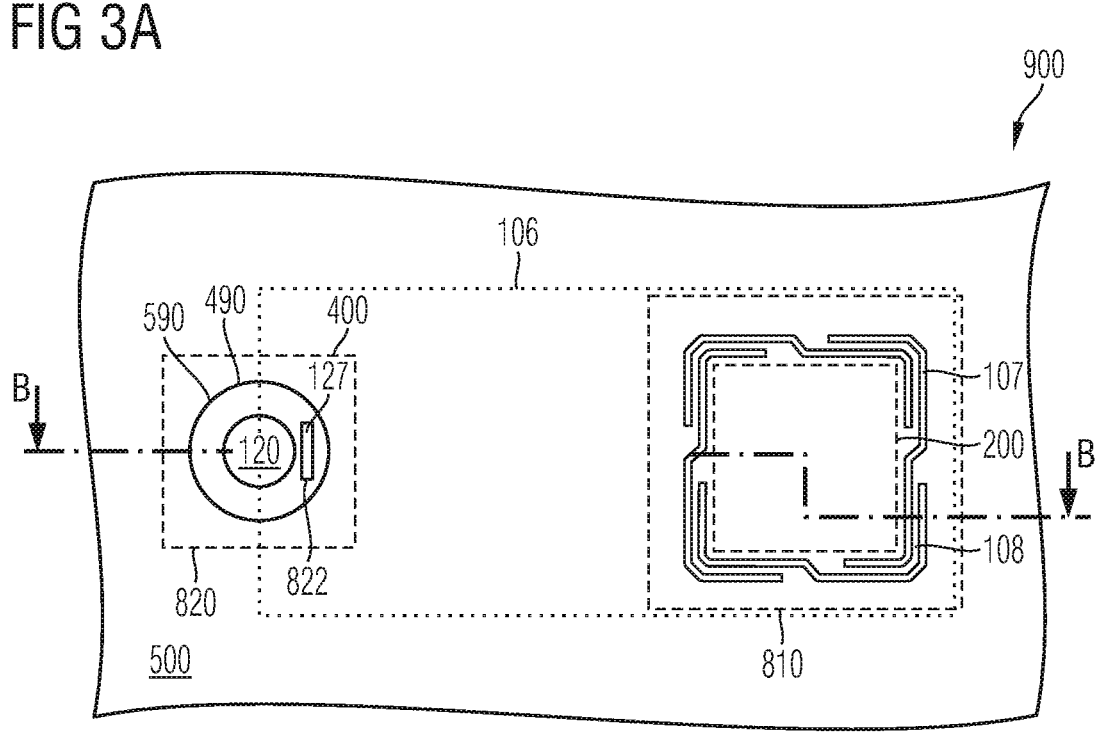
FIG. 3A is a schematic horizontal cross-sectional view of a portion of an integrated sensor device according to a further embodiment with the communicating channel formed in the sensor substrate.
Figure 3B:
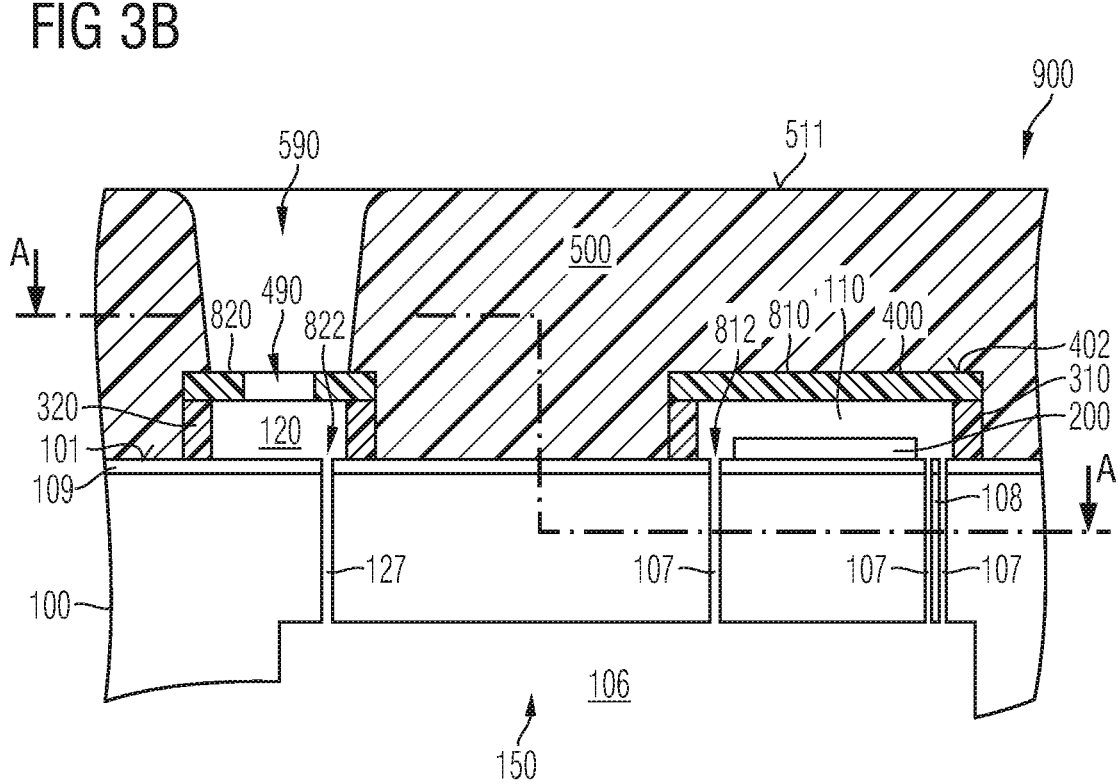
FIG. 3B is a schematic vertical cross-sectional view of the sensor device portion of FIG. 3A along line B-B.

The sensor device 900 of FIGS. 3A and 3B combines a communicating channel 150 using spring grooves 107 with an inlet box 820 formed adjacent to the sensor box 810 on the first surface 101 of a sensor substrate 100.

The frame structure 300 includes a second loop portion 320 that surrounds a second area 120 of the first surface 101. The second area 120 forms an inlet area. The lid structure 400 may partially cover the second loop portion 320 with the second area 120. A lid opening 490 in the lid structure 400 at least partially opens the inlet box 820. A mold compound 500 may vertically embed the inlet box 820 and the sensor box 810 on the first surface 101. A mold opening 590 may expose the lid opening 490. Alternatively, the mold compound 500 may be recessed and a final top surface 511 of the recessed mold compound may be coplanar with a top surface 402 of the lid structure 400.

A rear side cavity 106 may extend from the vertical projection of the sensor box 810 to the vertical projection of the inlet box 820. One or more connection grooves 127, which forms a base port 822 for the sensor box 810 and which may have the same vertical extension and the same width as the spring grooves 107, connect the rear side cavity 106 with the second area 120. A communicating channel 150, which includes the rear side cavity 106, the spring grooves 107 and the connection grooves 127, connects the first area 110 and the second area 120 and passes air or gas from the ambient to the first area 110. As in the embodiment of FIGS. 2A to 2C, the rear side cavity 106 takes part in piping gas or air from the ambient to the sensor box 810.

Figure 3C:
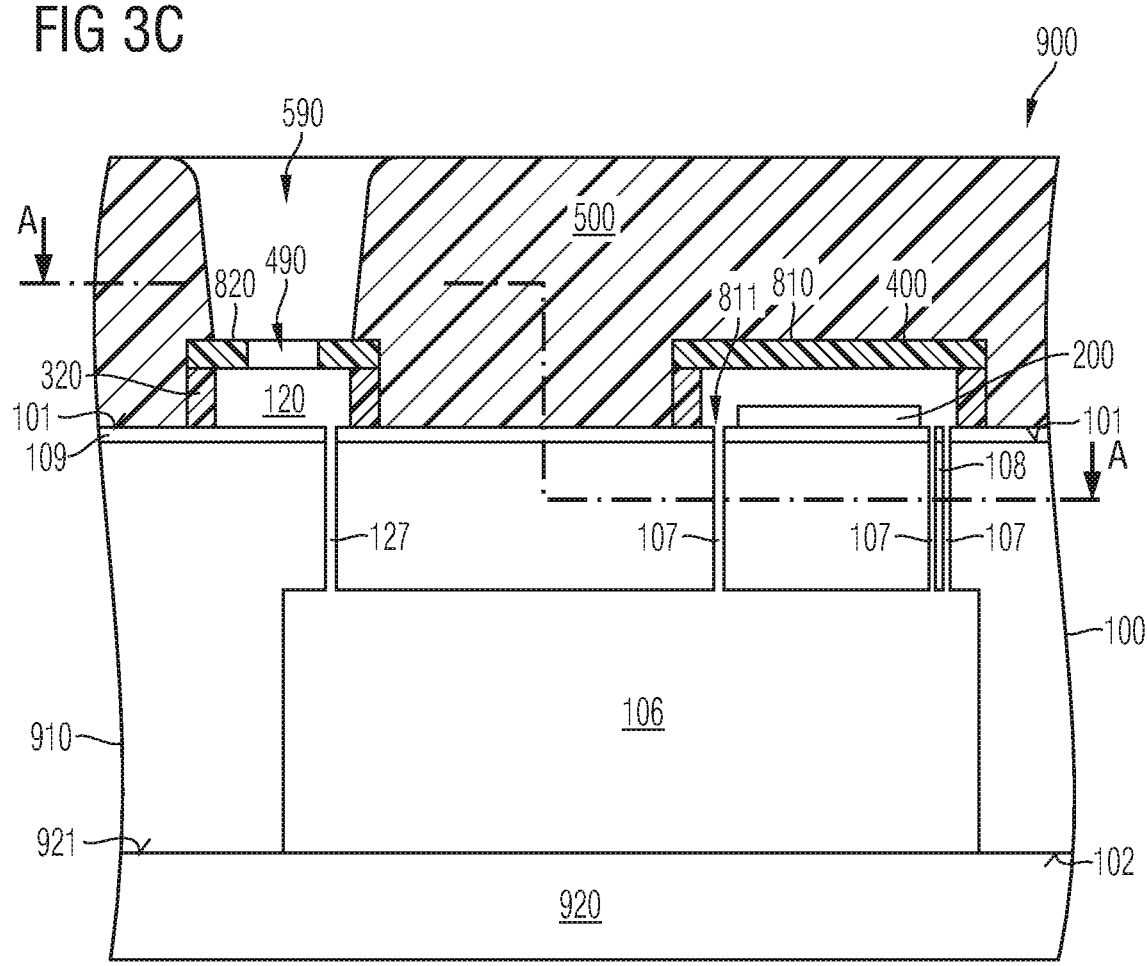
FIG. 3C is a schematic vertical cross-sectional view of a portion of a sensor device including the sensor device of FIGS. 3A to 3B and a carrier structure.

In FIG. 3C, the sensor device 900 includes a carrier structure 920 mounted on the second surface 102 of the sensor substrate 100 and closing the rear side cavity 106 on the back.

Figure 3D:
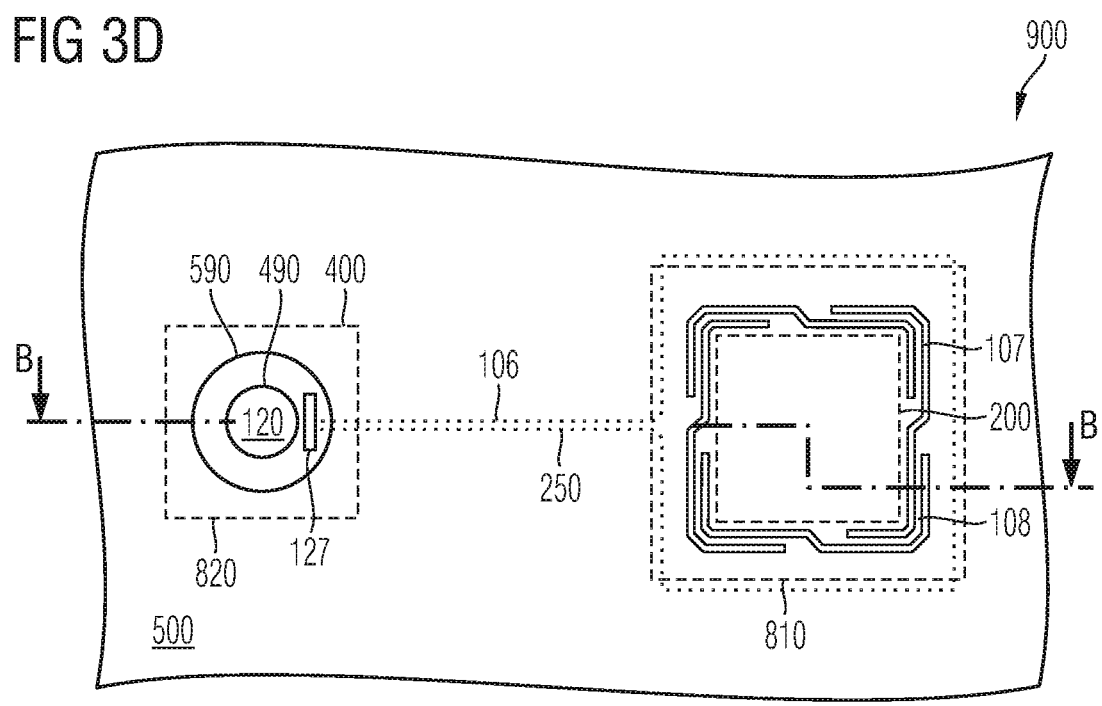
FIG. 3D is a schematic horizontal cross-sectional view of a portion of an integrated sensor device according to another embodiment with a portion of the communicating channel formed by a narrow portion of a rear side cavity.

In FIG. 3D, the rear side cavity 106 includes a narrow portion forming a substrate trench 250, which may have the same vertical extension as the rear side cavity 106. The substrate trench 250 may have a width in the order of magnitude of the spring grooves 107 and may extend from the vertical projection of the sensor box 810 to the connection grooves 127.

FIGS. 4A to 4D refer to different configurations of communicating channels 150 including substrate trenches 250 in the sensor substrate 100.

Figure 4A:
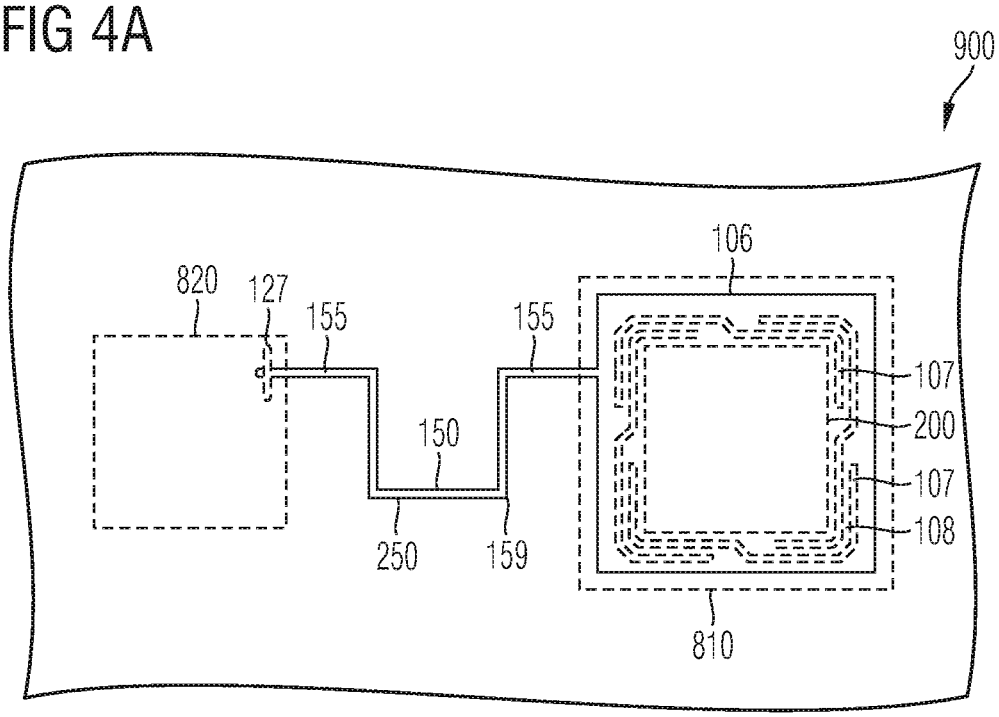
FIG. 4A is a schematic horizontal cross-sectional view of a portion of an integrated sensor device in the plane of a communicating channel according to an embodiment concerning a communicating channel with rectangular bends.

In FIG. 4A the portion of the communicating channel 150 including the substrate trench 250 includes four rectangular bends 159 and five orthogonal straight line sections 155, wherein the substrate trench 250 opens into a wide portion of the rear side cavity in the vertical projection of the sensor box 810 and exposing the spring grooves 107. The substrate trench 250 may have the same width along its complete horizontal longitudinal extension between the wide portion of the rear side cavity 106 and the connection groove 127 connecting the substrate trench 250 with the second area 120 of the inlet box 820.

Figure 4B:
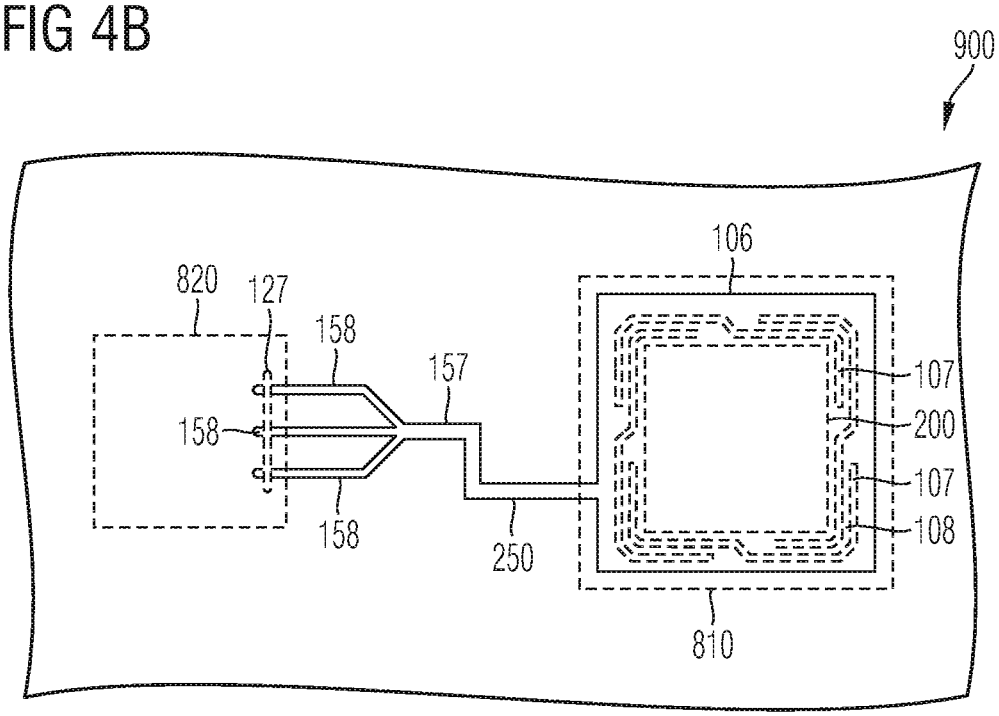
FIG. 4B is a schematic horizontal cross-sectional view of a portion of an integrated sensor device in the plane of the communicating channel according to an embodiment concerning a communicating channel with parallel narrow portions.

In the embodiment of FIG. 4B, the substrate trench 250 of the communicating channel 150 includes three narrow tubes 158 opening into a connection groove 127 and connected to one wide tube 157 opening into a wide portion of the rear side cavity 106.

Figure 4C:
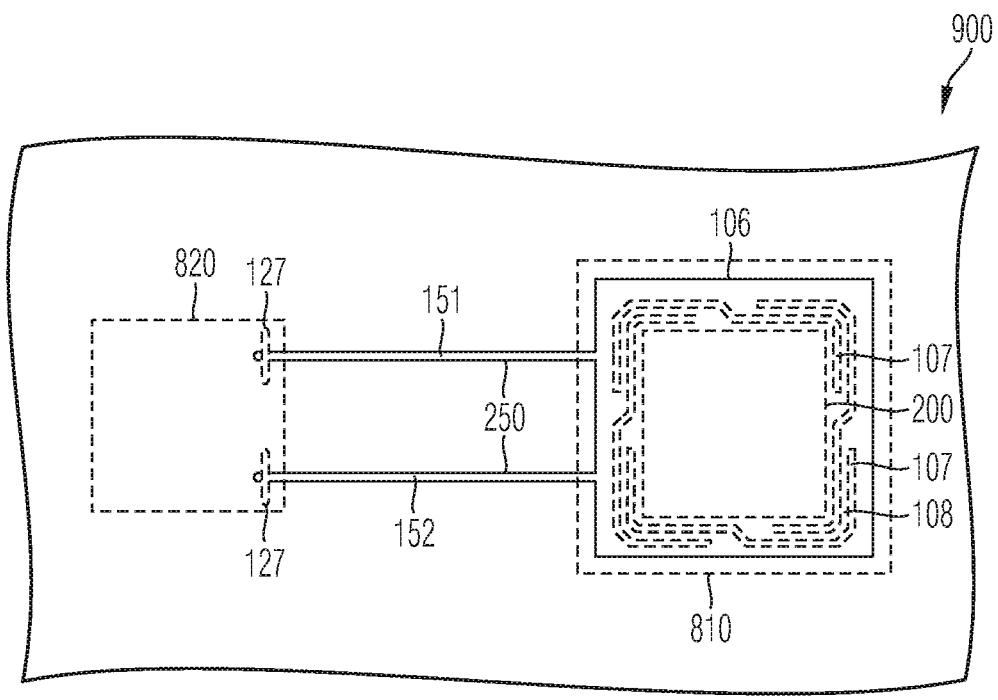
FIG. 4C is a schematic horizontal cross-sectional view of a portion of an integrated sensor device in the plane of the communicating channel according to an embodiment concerning a communicating channel including two parallel tubes.

The sensor device 900 of FIG. 4C includes a communicating channel 150 with a first tube 151 extending from a first connection groove 127, which opens into the inlet box 820, to a wide portion of the rear side cavity 106 in the vertical projection of the sensor box 810, and a second tube 152 extending from a second connection groove 127 opening into the inlet box 820 to the wide portion of the rear side cavity 106 in the vertical projection of the sensor box 810. The first tube 151 and the second tube 152 form part of the communicating channel 150. With increasing number of parallel tubes, the probability for that the communicating channel 150 gets clogged decreases.

Figure 5A:
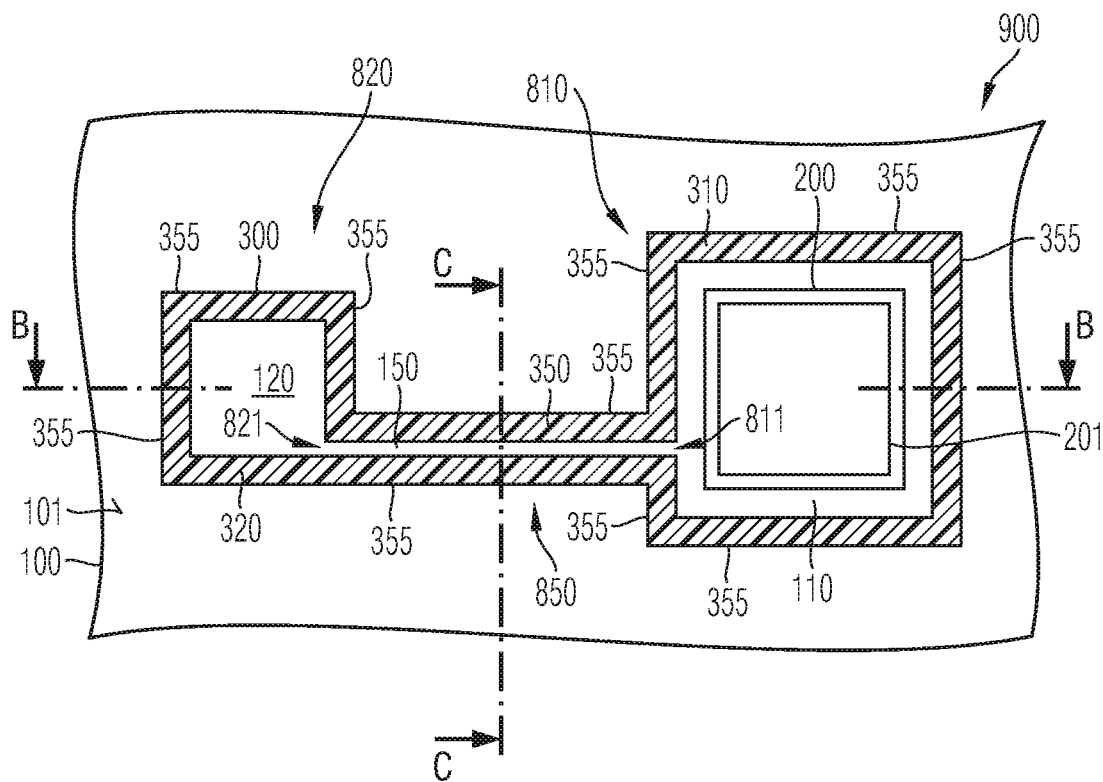
FIG. 5A is a schematic horizontal cross-sectional view of a portion of an integrated sensor device with a frame structure surrounding a sensor area, an inlet area and a channel connecting the inlet area and the sensor area according to an embodiment.
Figure 5B:
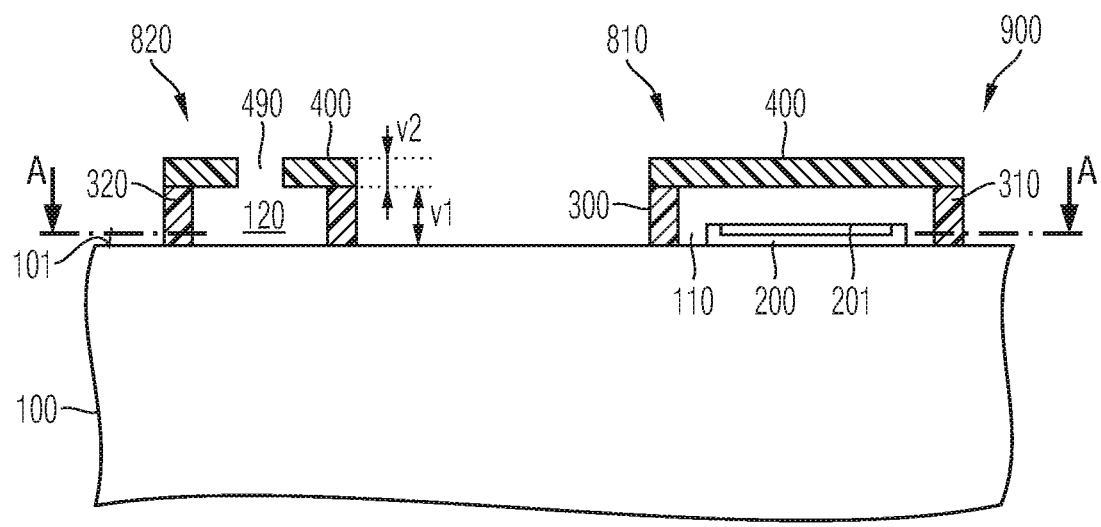
FIG. 5B is a schematic vertical cross-sectional view of the sensor device portion of FIG. 5A along line B-B.
Figure 5C:
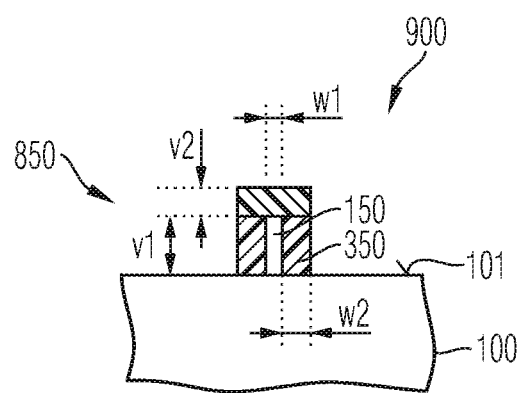
FIG. 5C is a schematic vertical cross-sectional view of the sensor device portion of FIG. 5A along line C-C.

FIGS. 5A to 5C illustrate a lateral, side-by-side arrangement of a sensor box 810, an inlet box 820, and a conduit 850 on a first surface 101 of a sensor substrate 100. The sensor box 810 encases a sensor unit 200. The inlet box 820 provides an opening to the ambient. The conduit 850 conducts a gaseous medium from the inlet box 820 to the sensor unit 200 in the sensor box 810.

As regards the inlet box 820 and the sensor box 810 reference is made to the description above.

A connection portion 350 complements the first loop portion 310 and the second loop portion 320 to a complete frame and forms a communicating channel 150 that connects the first area 110 through a lateral port 811 in the first loop portion 310 with the second area 120 through a lateral port 821 in the second loop portion 320.

The lid structure 400 further completely covers the connection portion 350 with the communicating channel 150 such that the lid structure 400 and the connection portion 350 form a conduit 850 connecting the sensor box 810 with an inlet box 820 formed by the second loop portion 320 partially covered by the lid structure 400. The first and second loop portions 310, 320 may be formed from straight line sections 355. Horizontal cross-sections of the first and second areas 110, 120 may be polygons, e.g. rectangles.

The communicating channel 150 may have a uniform first width w1 or may have at least one narrow section with the first width w1 in a range from 3 μm to 100 μm, for example in a range from 5 μm to 10 μm. A line width w2 of the line sections 355 may be in a range from 20 μm to 100 μm, for example, in a range from 30 μm to 60 μm.

The lateral arrangement of the inlet box 820 with regard to the sensor box 810 avoids that particles contained in the gaseous medium the sensor unit 200 is exposed to get into touch with the sensitive surface 201. In addition, the narrow communicating channel 150 blocks the access of particles of critical dimensions to the sensor box.

Since the lid structure 400 can be formed with a comparatively small vertical extension v2, protection of the sensor unit 200 against critical particles gets along without significant increase of the overall device thickness as it is the case if sensor particle protection provides a mechanical shield or grid mounted above the sensor unit by a wafer bonding process or by a customized packaging process which further significantly increases device costs and package process complexity. By contrast, the lateral decoupling of inlet box 820 and sensor box 810 achieves reliable particle protection at only moderate increase of device height and only moderate increase of process complexity, because the frame structure 300 and the lid structure 400 can be formed by low-cost wafer level processing.

FIGS. 5A to 5C may illustrate inlet box 820, conduit 850 and sensor box 810 formed in one of a plurality of device regions on a semiconductor wafer before dicing the semiconductor wafer into a plurality of identical sensors dies. FIGS. 5A to 5C may further refer to single sensor dies after dicing and before packaging and may also illustrate a completed sensor device 900, wherein illustration of further components such as contact pads, bond wires and mold compound is omitted for illustrative purposes.

FIGS. 6A to 6D refer to a finalized sensor device 900 after packaging.

The sensor substrate 100 may include a semiconductor layer 104 of a crystalline semiconductor material such as silicon (Si), germanium (Ge), silicon germanium (SiGe), silicon carbide (SiC) or any AIIIBV semiconductor. In the semiconductor layer 104 electronic elements 105 are formed, for example, a read-out circuit for amplifying an electric signal generated by a sensor unit 200 and containing information about a gaseous medium to which a sensitive surface 201 of the sensor unit 200 is exposed.

The sensor substrate 100 further includes an outermost passivation layer 109 from one or more dielectric materials. The outermost passivation layer 109 may be a uniform layer or may be a layer stack from different materials such as thermally grown silicon oxide, silicon nitride, silicon oxynitride, deposited silicon oxide, for example, silicon oxide formed by using TEOS (tetraethylorthosilicate) as precursor material, undoped silicate glass or a doped silicate glass such as BSG (boron silicate glass), PSG (phosphorus silicate glass), BPSG (boron phosphorus silicate glass), FSG (fluorine silicate glass) or spin-on glass. A horizontal cross-section of the sensor substrate 100 may be a rectangle with an area in a range from 0.5 mm2 to 2 cm2, e.g. in a range from 1 mm2 to 1 cm2.

On the outermost passivation layer 109 a first area includes a sensor unit 200, which may be a pressure sensor or a gas sensor. The sensor unit 200 is electrically connected to the electronic elements 105 in the semiconductor layer 104. Contact pads 190 directly on the outermost passivation layer 109 or laterally embedded in the outermost passivation layer 109 are electrically connected to the sensor unit 200 and/or to the electronic elements 105 in the semiconductor layer 104. Bond wires 196 electrically connect the contact pads 190 with conductive leads of a packaging of the sensor device 900.

A reflective structure 195 in a second area laterally spaced from the first area may be from the same material as the contact pads 190 or from another material. The reflective structure 195 is from a material suitable for reflecting laser beams at high reflectivity.

A frame structure 300 and a lid structure 400 as described above form a sensor box 810 encasing the first area with the sensor unit 200, an inlet box 820 encasing the second area with the reflective structure 195 and a conduit 850 with a communicating channel 150. The inlet box 820 has a lid opening 490 in the lid structure 400. The lid opening 490 allows gas to enter the inlet box 820 and the communicating channel 150 pipes the gas to the sensor box 810.

A mold compound 500 from, for example, a resin laterally and vertically embeds the bond wires 196, the conduit 850 and the sensor box 810. In the vertical projection of the inlet box 820, a mold opening 590 exposes the lid opening 490.

Figure 6A:
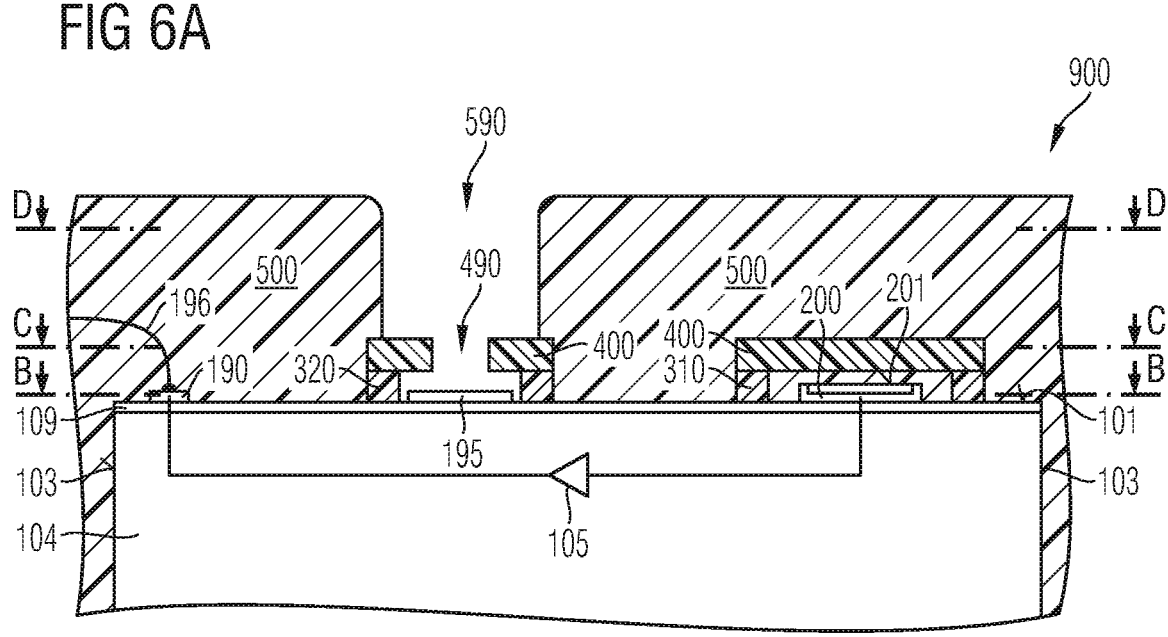
FIG. 6A is a schematic vertical cross-sectional view of an integrated sensor device according to an embodiment including a frame structure, a lid structure, and a mold compound with mold opening.
Figure 6B:
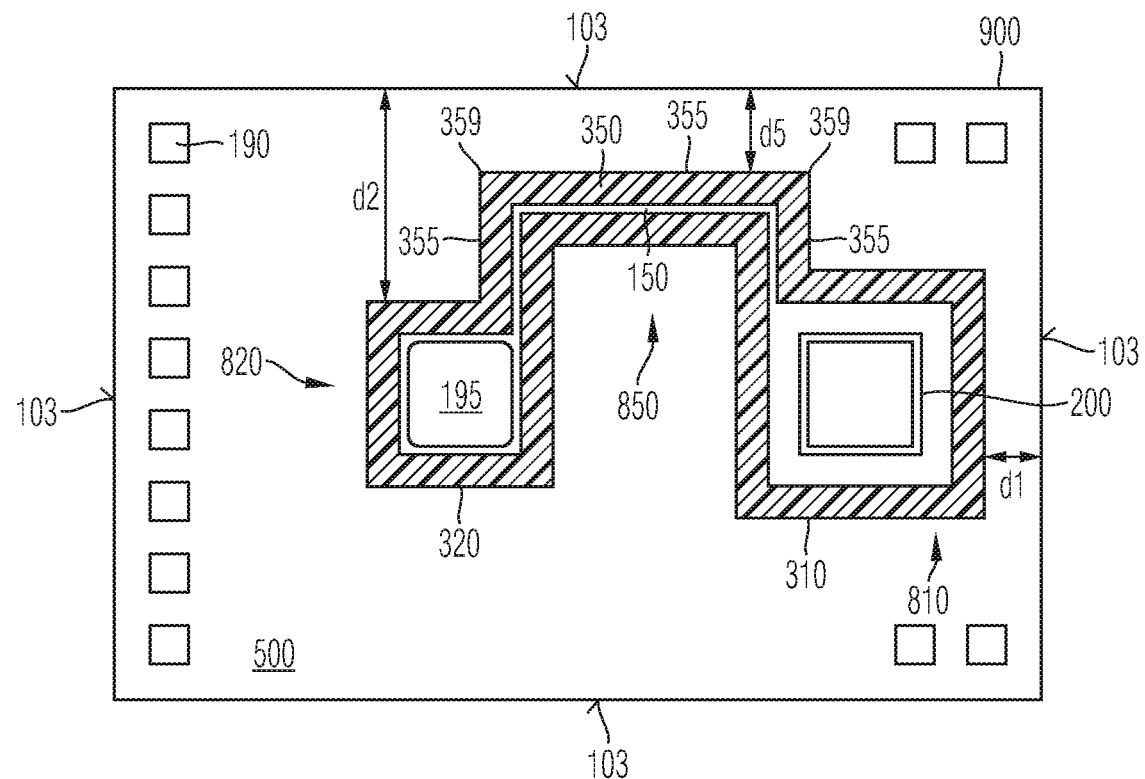
FIG. 6B is a schematic horizontal cross-sectional view of the integrated sensor device of FIG. 6A along line B-B through the frame structure.

FIG. 6B is a horizontal cross-section through the frame structure 300 that includes a connection portion 350 with two rectangular bends 359 and three pairs of parallel line sections 355. The inlet box 820 may be formed at a sufficient distance to an outer lateral surface 103 of the sensor substrate 100 and outside of a vertical projection of the contact pads 190. For example, a minimum distance d2 between the closest outer lateral surface 103 and the second loop portion 320 of the frame structure 300 is at least 50 μm. A minimum distance d1 between the closest outer lateral surface 103 and the first loop portion 310 and a minimum distances d5 between the closest outer lateral surface 103 and the connection portion 350 may be at least 15 μM.

Figure 6C:
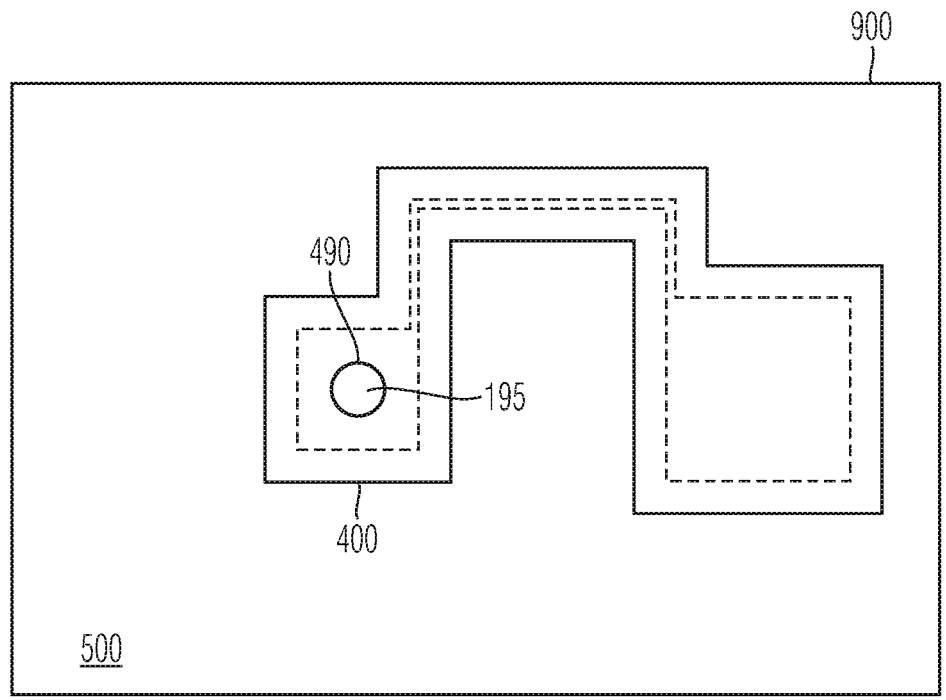
FIG. 6C is a schematic horizontal cross-sectional view of the integrated sensor device of FIG. 6A along line C-C through the lid structure.

FIG. 6C shows a horizontal cross-section in the plane of the lid structure 400. The lid opening 490 exposes the second area 120 enclosed by the second loop portion 320 of the frame structure 300 in the vertical projection of the reflective structure 195. A horizontal cross-section of the lid opening 490 may be an irregular or regular polygon with or without rounded or chamfered edges, for example, a rectangle, or an ellipse, an oval or a circle. The illustrated embodiment shows a circular lid opening 490 with a diameter of at least 50 µm and at most 500 µm, for example in a range from 100 µm to 200 µM.

Figure 6D:
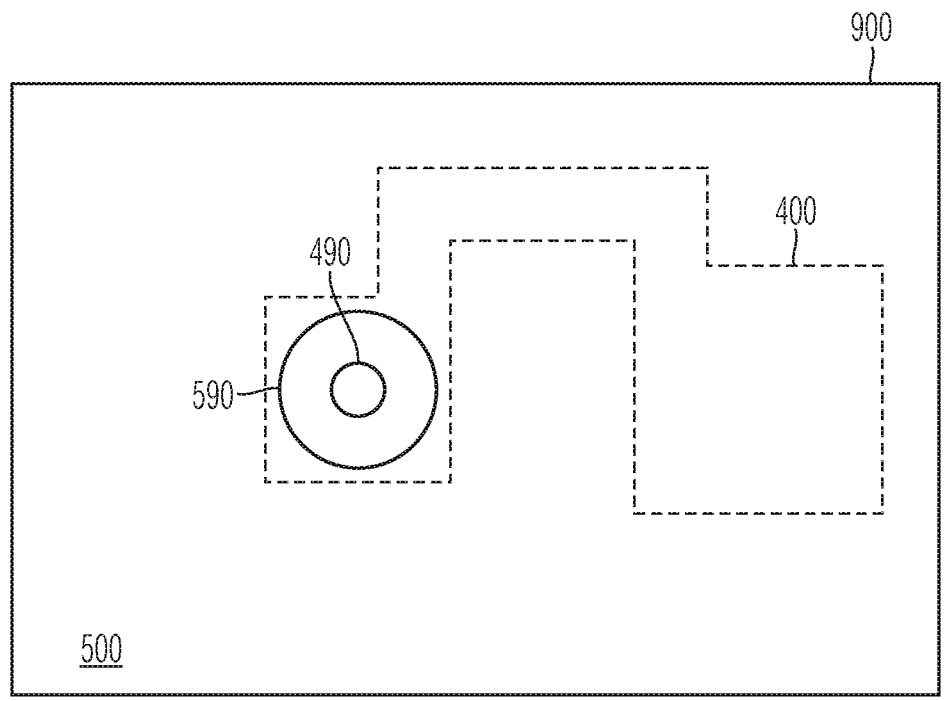
FIG. 6D is a schematic horizontal cross-sectional view of the integrated sensor device of FIG. 6A along line D-D through the mold compound.

According to FIG. 6D a mold opening 590 that exposes the lid opening 490 may have the same horizontal cross-sectional shape and a greater minimum diameter than the lid opening 490.

Figure 7A:
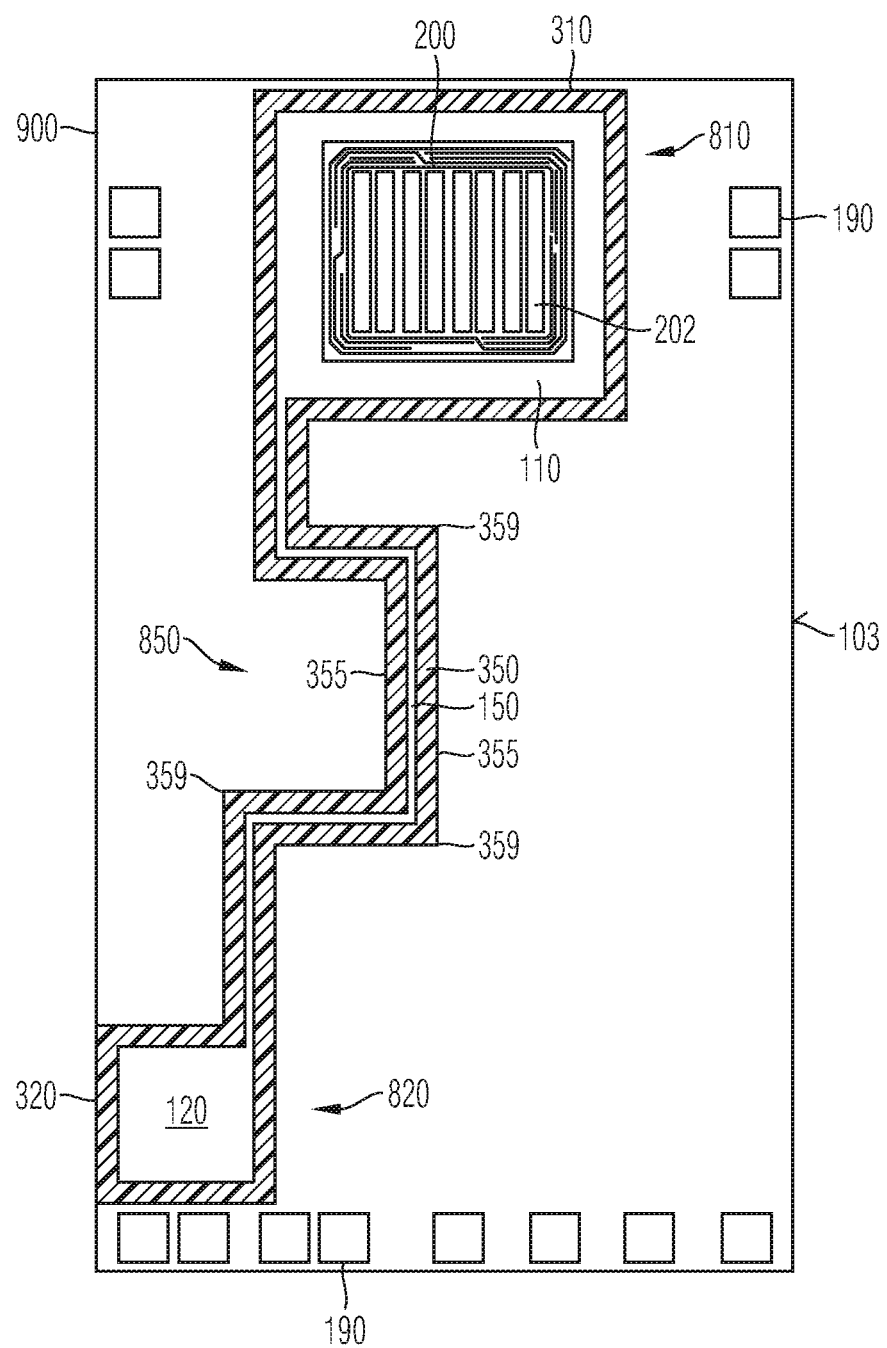
FIG. 7A is a schematic horizontal cross-sectional view of an integrated sensor device in the plane of the frame structure according to a further embodiment.
Figure 7B:
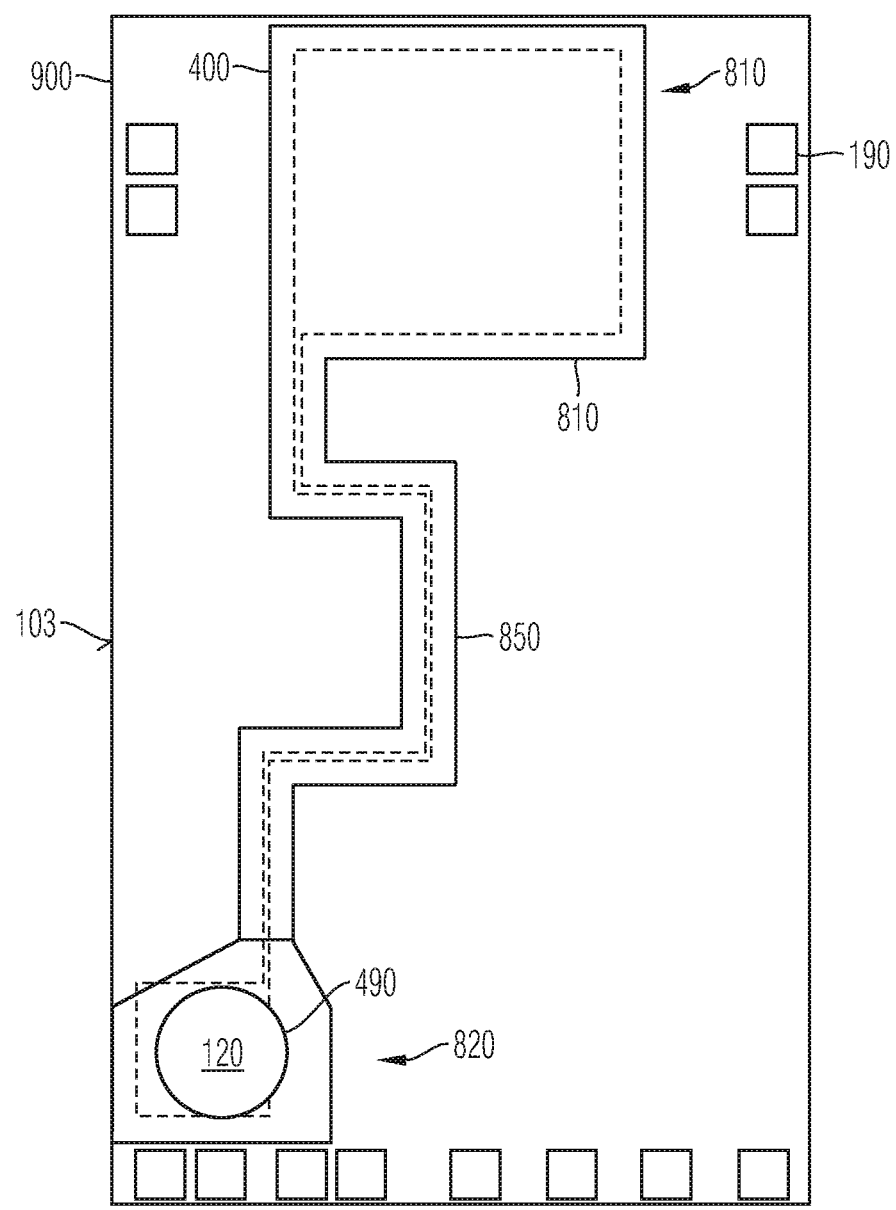
FIG. 7B is a schematic horizontal cross-sectional view of the integrated sensor device of FIG. 7A in the plane of the lid structure.

FIGS. 7A to 7B show a further embodiment of a sensor device 900. The sensor unit 200 is a pressure sensor with eight suspended membranes 202 arranged parallel to each other. The suspended membranes 202 span across one or more hermetically closed cavities with defined air pressure. A vertical deflection of the suspended membranes 202 is proportional to the ambient pressure. The suspended membranes 202 may include a metallic component forming an electrode of a sensor capacitor. A read-out circuit, which may be integrated in the sensor substrate 100, transforms the change of the capacity of the sensor capacitor into a measurement signal.

The connection portion 350 of the frame structure 300 includes four rectangular bends 359 and five pairs of parallel line sections 355.

FIG. 7B shows a circular lid opening 490 in the lid structure 400. The circular lid opening 490 may be formed by irradiating a laser beam onto the lid structure 400. The laser beam may be an UV (ultraviolet) laser or a carbon dioxide laser.

FIGS. 8A to 8G refer to different configurations of the connection portion 350 of the frame structure 300 and of the communicating channel iso.

Figure 8A:
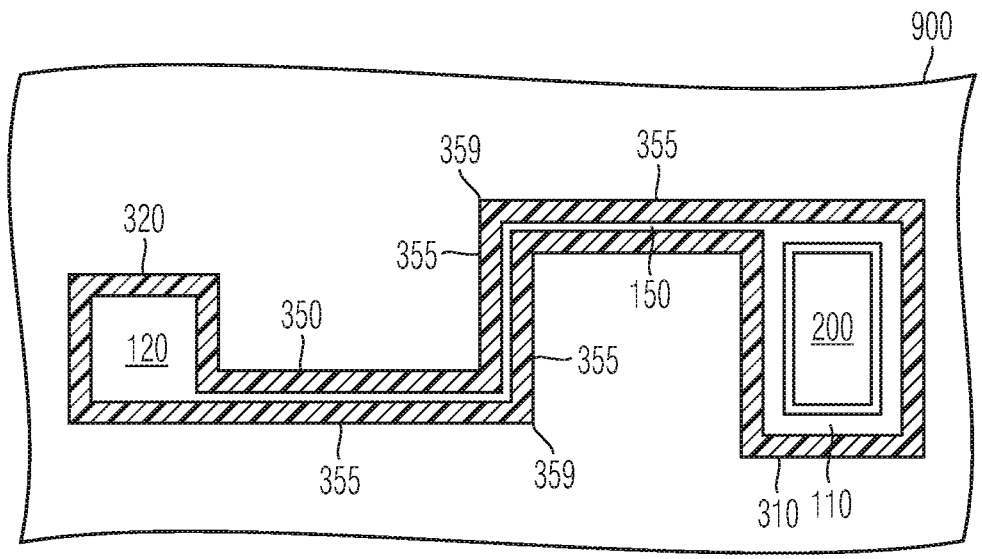
FIG. 8A is a schematic horizontal cross-sectional view of a portion of an integrated sensor device in the plane of the frame structure according to an embodiment concerning a communicating channel with two rectangular bends.

In FIG. 8A the communicating channel 150 opens out into the first area 110 and into the second area 120 in a way that outer sidewalls of line sections 355 of the connection portion 350 and the first and second loop portions 310, 320 are flush and in one vertical plane. Three pairs of line sections 355 form two rectangular bends 359. The communicating channel 150 has the same cross-sectional area along the complete extension of the communicating channel 150 from a port opening into the sensor box encasing the first area 110 to a port opening into the inlet box encasing the second area 120.

Figure 8B:
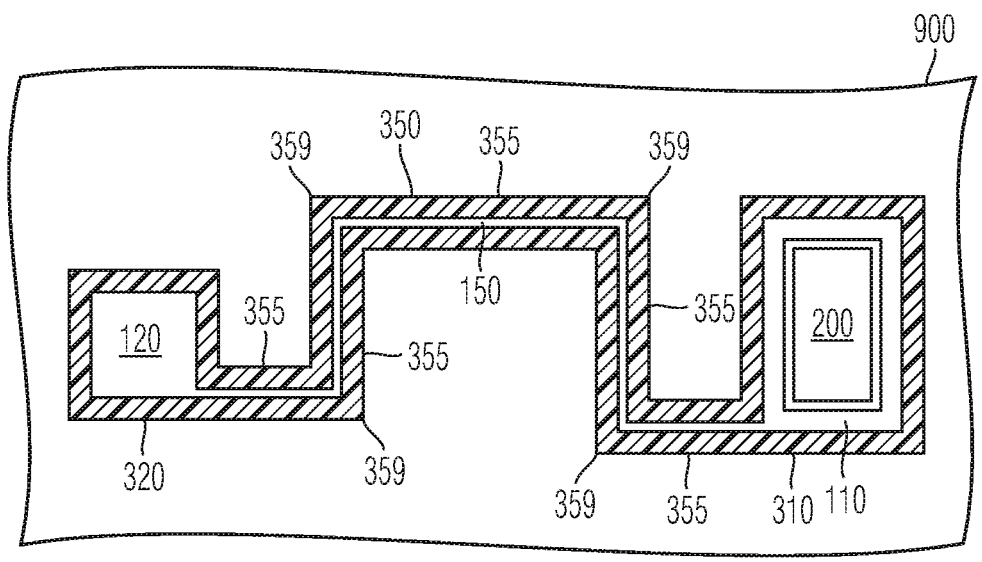
FIG. 8B is a schematic horizontal cross-sectional view of a portion of an integrated sensor device in the plane of the frame structure according to an embodiment concerning a meandering communicating channel with four rectangular bends.

In FIG. 8B the sensor device 900 includes a connection portion 350 with four rectangular bends 359 and five pairs of parallel line sections 355 that form a meandering loop between the first loop portion 310 and the second loop portion 320.

In the previous examples, the communicating channel 150 consists of one single tube. According to other embodiments, the communicating channel 150 may include two, three or more tubes conducting the gaseous medium at least in sections in parallel branches between the inlet box and the sensor box.

As a simplified embodiment for a connection portion 350 with more than one tube, FIG. 8C shows a connection portion 350 with a first branch 351 encasing a first tube 151, which extends from a port opening into the inlet box to a port opening into the sensor box, and a second branch 352 encasing a second tube 152, which extends from another port opening into the inlet box to another port opening into the sensor box. The first tube 151 and the second tube 152 form the communicating channel 150. With increasing number of parallel branches, the probability for that the communicating channel 150 gets clogged and for that agglomerating particles block a gaseous medium from passing the communicating channel 150 decreases.

In the previous embodiments, a vertical cross-sectional area of the communicating channel 150 is uniform across the complete length from the inlet box to the sensor box.

FIG. 8D shows a connection portion 350 with wide sections 357 that form wide tubes 157 and one narrow section 358 that forms a narrow tube 158. The cross-sectional area of the narrow tube 158 may be in a range from, e.g., about 3 µm×10 µm to 6 µm×20 µM and the cross-sectional area of the wide tubes 157 may be at least twice, five times or at least ten times the cross-sectional area of the narrow tube 158 such that unwanted deviations of the lateral extension of the connection portion 350 of the frame structure 300 do not adversely impact device reliability.

The concept of wide and narrow tubes of FIG. 8D may be combined with the concept of redundant branches of FIG. 8C such that the connection portion 350 forms a sort of lateral grid.

Figure 8E:
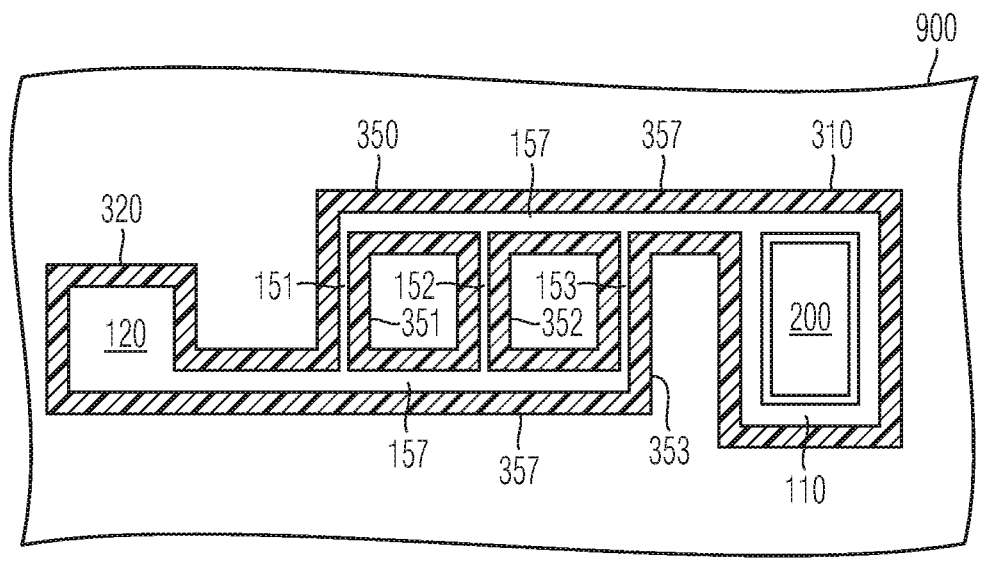
FIG. 8E is a schematic horizontal cross-sectional view of a portion of an integrated sensor device in the plane of the frame structure according to an embodiment concerning a communicating channel with parallel narrow portions.

In FIG. 8E three parallel narrow first, second and third branches 351, 352, 353 connect two wide sections 357, wherein a first wide tube 157 connects a narrow first tube 151, a narrow second tube 152, and a narrow third tube 153 with the sensor box and a second wide tube 157 connects the first, second and third tubes 151, 152, 153 with the inlet box. The communicating channel 150 partially splits up in three parallel, narrow first, second and third tubes 151, 152, 153.

Figure 8F:
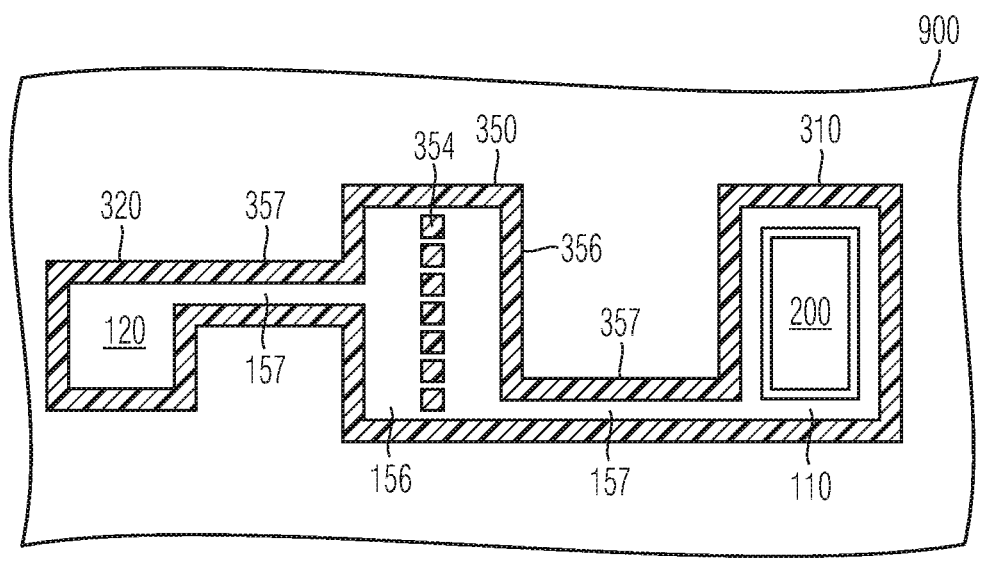
FIG. 8F is a schematic horizontal cross-sectional view of a portion of an integrated sensor device in the plane of the frame structure according to an embodiment with a communicating channel including a filter box.

In FIG. 8F the connection portion 350 includes a third loop portion 356 surrounding a filter area 156. In the filter area 156 vertical columns of the material of the frame structure 300 may form a lateral grid 354. Wide sections 357 may connect the third loop portion 356, which defines a filter box, with the sensor box and the inlet box.

The connection portion 350 may include a communicating channel 150 that connects one single inlet box with one single sensor box. According to other embodiments the communicating channel 150 pipes gas from one single inlet box to two or more sensor boxes, from two or more inlet boxes to one single sensor box or from two or more inlet boxes to two or more sensor boxes.

Figure 8G:
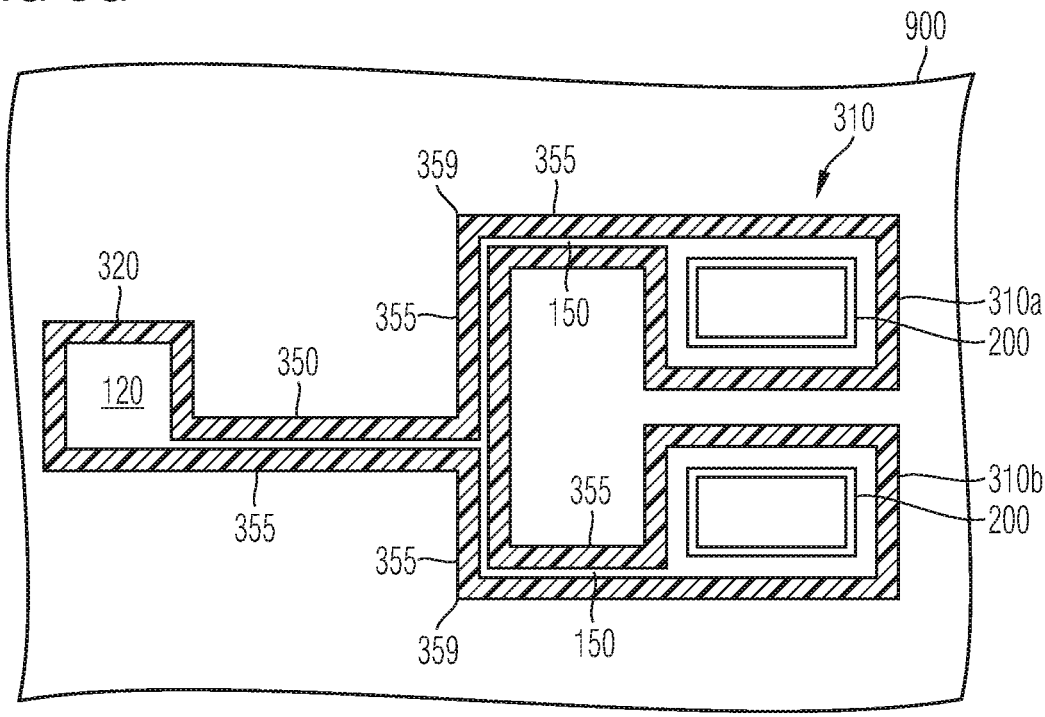
FIG. 8G is a schematic horizontal cross-sectional view of a portion of an integrated sensor device in the plane of the frame structure according to an embodiment with a communicating channel to two sensor boxes.

In FIG. 8G the first loop portion 310 includes two separated sub-portions 310a, 310b and the communicating channel 150 connects one second loop portion 320 with both sub-portions 310a, 310b of the first loop portion 310. The first and second sub-portions 310a, 310b may encompass sensor units 200 of different sensitivity.

Figure 8H:
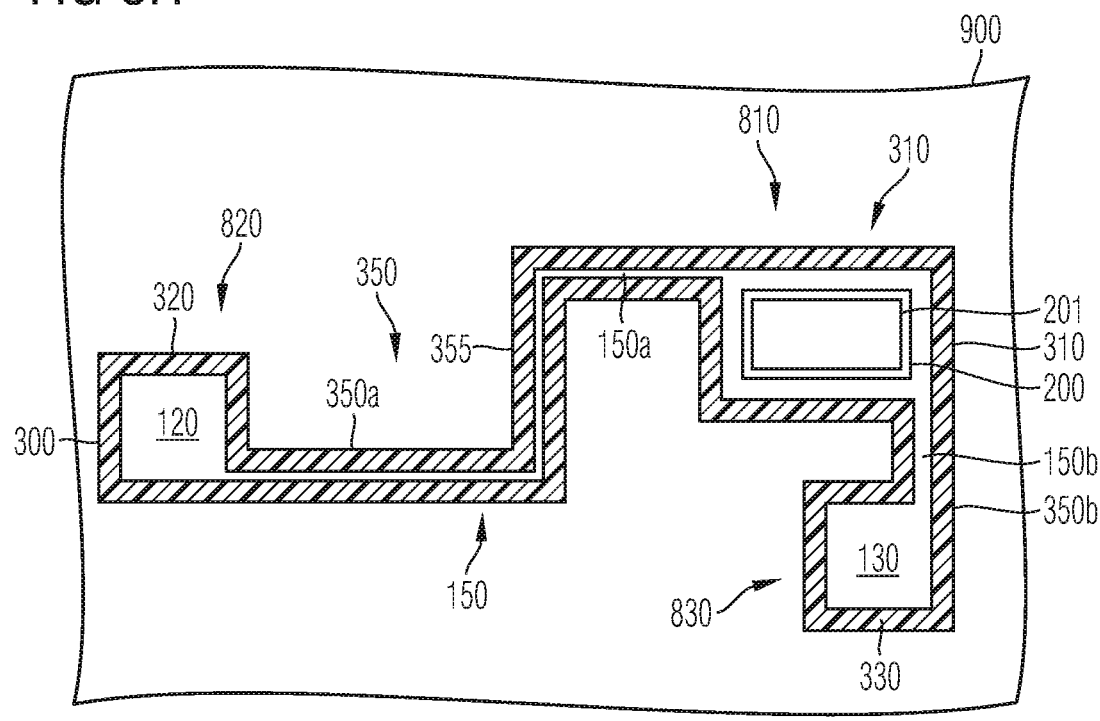
FIG. 8H is a schematic horizontal cross-sectional view of a portion of an integrated sensor device in the plane of the frame structure according to an embodiment concerning a gas sensor with an outlet box.

FIG. 8H shows a frame structure 300 of a sensor device 900 which sensor unit 200 is a gas sensor with a sensitive surface 201 that includes receptor sites for one or more species of molecules. A third loop portion 330 of the frame structure 300 encompasses a third area 130 effective as outlet area. The third loop portion 330 is part of an outlet box 830 providing a further opening to the ambient. Gas enters the frame structure 300 through an opening in a lid structure 400 partly covering the second area 120, passes a first section 350a of a connection portion 350 with a first section 150a of a communicating channel 150 and reaches the sensor box 810. The gas leaves the sensor box 810 through a second section 350b of the connection portion 350 with a second section 150b of the communicating channel 150 and may leave the frame structure 300 through a further opening in the lid structure 400 partly covering the outlet box 830.

According to another embodiment, inlet box 820 or outlet box 830 may be replaced by an access or exit through the sensor substrate 100 as described with reference to FIGS. 2A to 4C.

The sensor box 810, the inlet box 820 and the conduit 850 of the previous Figures may be provided from different materials in different ways, e.g., by 3D-printing.

FIGS. 9A to 14B refer to a method for forming the sensor box 810, the conduit 850 and the inlet box 820 of the previous Figures from photoresistive material.

Figure 9A:
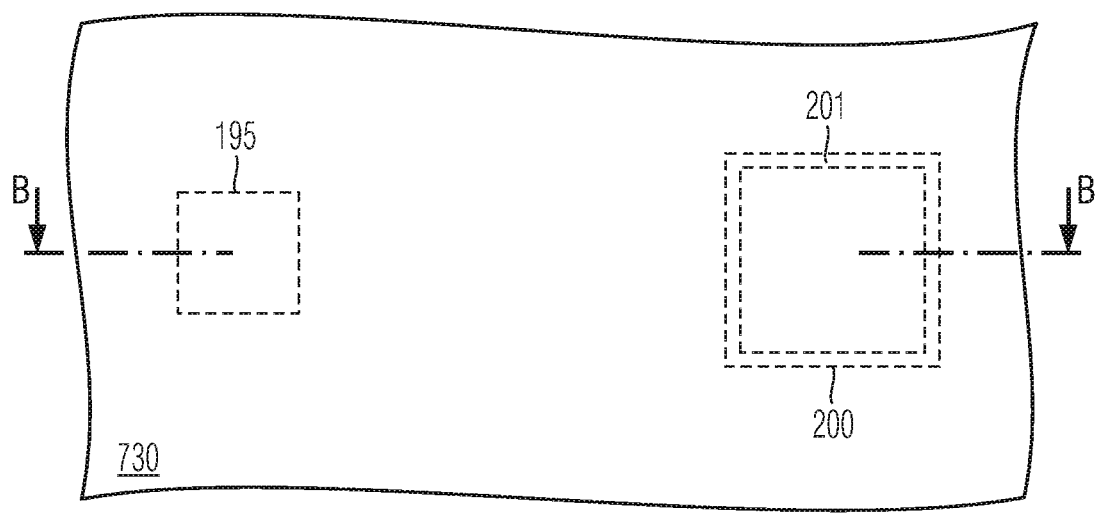
FIG. 9A is a schematic plan view of a portion of a semiconductor substrate including sensor units on a front surface for illustrating a method of manufacturing integrated sensor devices, after forming a photoresist layer on a front side.
Figure 9B:
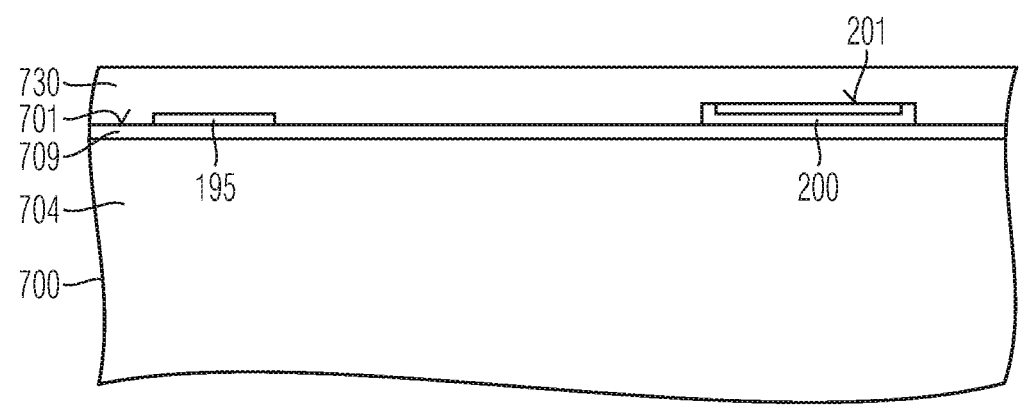
FIG. 9B is a schematic vertical cross-sectional view of the semiconductor substrate portion of FIG. 9A.

FIGS. 9A and 9B show a semiconductor substrate 700 that includes a semiconductor layer 704 of crystalline semiconductor material, for example Si, Ge, SiGe, SiC or an AIIIBV semiconductor. The semiconductor substrate 700 may be a silicon wafer, which planar front surface 701 may be formed by a topmost passivation layer 709.

Shape, dimensions and material of the semiconductor substrate 700 are compatible with production lines for silicon-based semiconductor devices. For example the semiconductor substrate 700 is a wafer with an approximately cylindrical shape, wherein a diameter of the wafer is at least 150 mm, e.g., 200 mm ("8 inch"), 300 mm ("12 inch"), or 450 mm ("18 inch"). A thickness of the semiconductor substrate 700 may be between 100 μm and several millimeters, e.g., in a range from 200 μM to 1 mm, by way of example. A normal to the front surface 701 defines a vertical direction. Directions parallel to the front surface 701 are horizontal directions. In the semiconductor layer 704 at least connection lines are formed that are accessible through the front surface 701. According to an embodiment, electronic elements of electronic circuits such as read-out circuits and interface circuits are formed in the semiconductor layer 704.

On the front surface 701 a sensor unit 200 is formed by typical BEOL processes in a first area, wherein conductive structures in the sensor unit 200 like capacitor electrodes are electrically connected to the connection lines in the semiconductor layer 704. A reflective structure 195 may be formed by BEOL processes in a second area on the front surface 701 side-by-side with and spaced from the sensor unit 200, e.g., contemporaneously with contact pads.

A liquid containing a first photoresist material and a solvent is spun on the front surface 701 such that the liquid covers the sensor unit 200 and the reflective structure 195. After applying the liquid containing the first photoresist material, a soft-bake step evaporates a portion of the solvent to stabilize the photoresist material before an exposure step. According to another embodiment a resist laminate may be attached onto the front surface 701.

FIGS. 9A and 9B show a photoresist layer 730 of uniform height formed from the dried photoresist material or from the attached resist laminate. The photoresist layer 730 covers the front surface 701 and embeds completely the sensor unit 200 and the reflective structure 195. The first photoresist material may be a negative resist including soluble light- and/or energy-sensitive polymers that change from unpolymerized to polymerized by exposure to light or to another radiation, wherein the polymers form a cross-linked species of higher etch-resistivity than the unpolymerized species.

The photoresist layer 730 is aligned to a reticle and exposed to light passing the reticle and irradiating selective portions of the photoresist layer 730. In the irradiated portions the first photoresist material in the photoresist layer 730 polymerizes. A developing step may apply a developer liquid that selectively solves the unpolymerized portions of the photoresist layer 730.

Figure 10A:
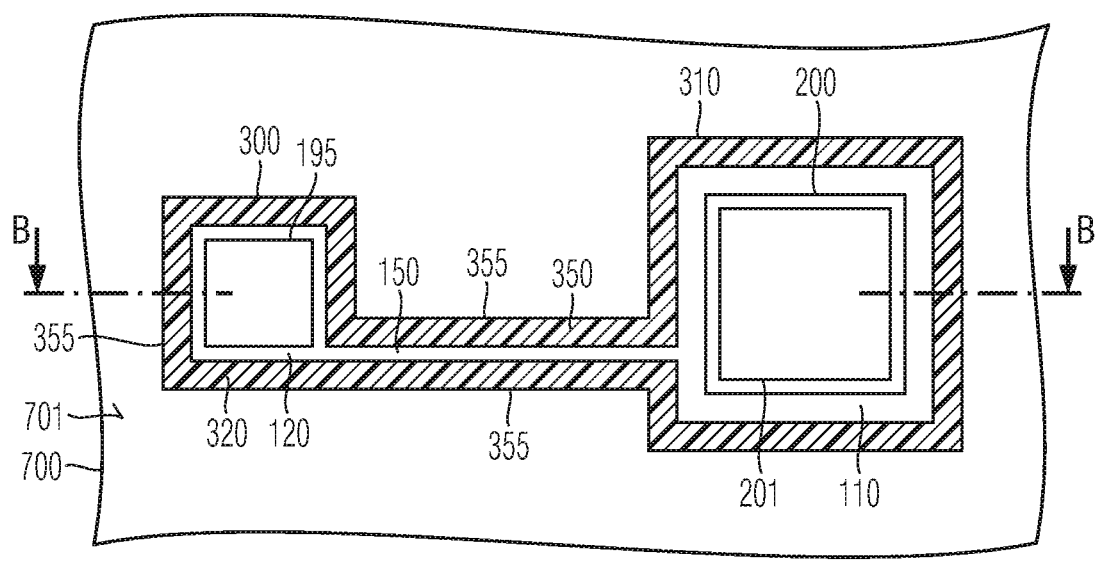
FIG. 10A is a schematic plan view of the semiconductor substrate portion of FIG. 9A, after forming a frame structure from the photoresist layer.
Figure 10B:
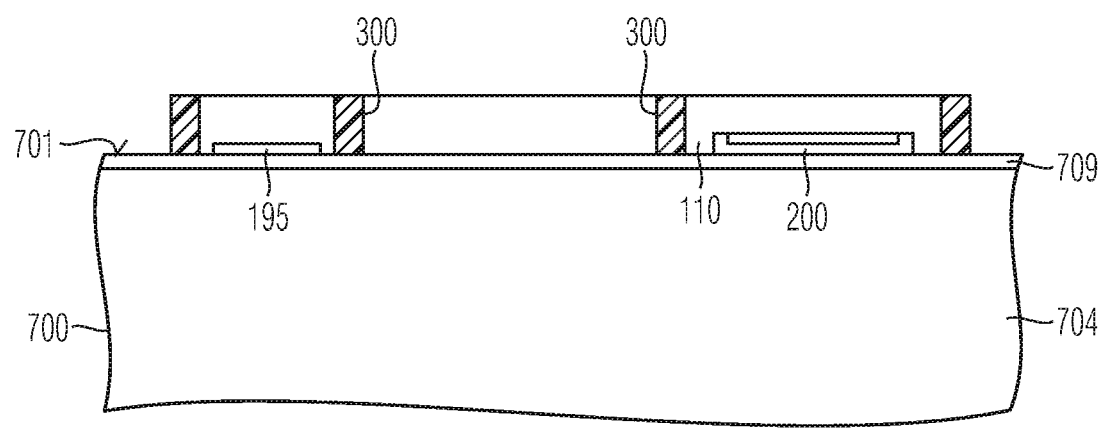
FIG. 10B is a schematic vertical cross-sectional view of the semiconductor substrate portion of FIG. 10A.

FIGS. 10A and 10B show the polymerized portions of the first photoresist material forming a frame structure 300. The frame structure 300 includes a first loop portion 310 laterally surrounding the sensor unit 200 in the first area 110 of the front surface 701, a second loop portion 320 laterally enclosing the second area 120 and a connection portion 350 forming a communicating channel 150 between the first area 110 and the second area 120.

A photoresist laminate 740 of a second photoresist material is spanned across the semiconductor substrate 700 and bonded or adhered on top of the frame structure 300.

Figure 11A:
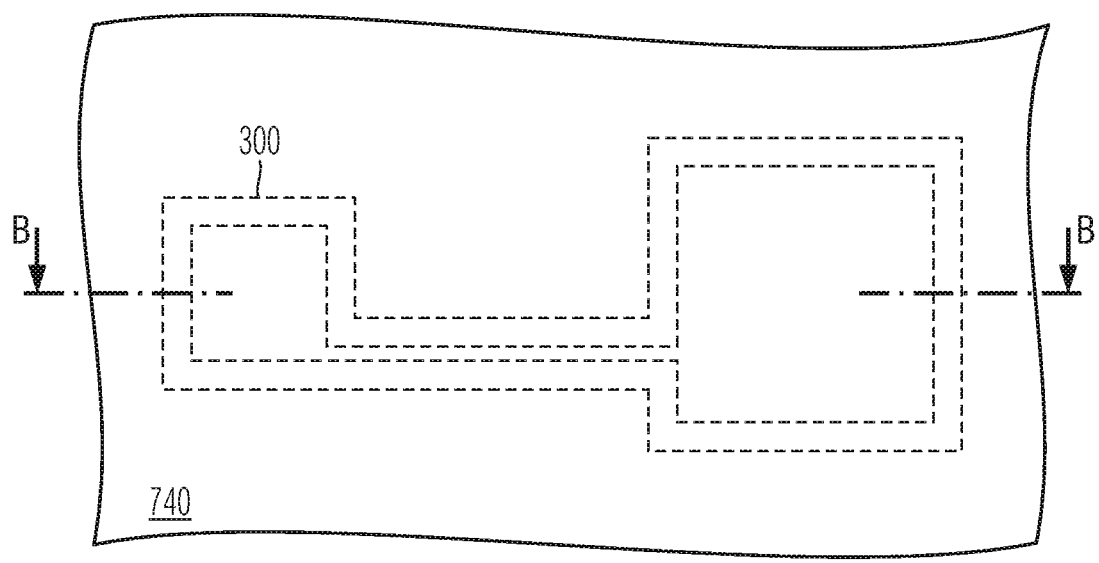
FIG. 11A is a schematic plan view of the semiconductor substrate portion of FIG. 10A, after applying a photoresist laminate on the frame structure.
Figure 11B:
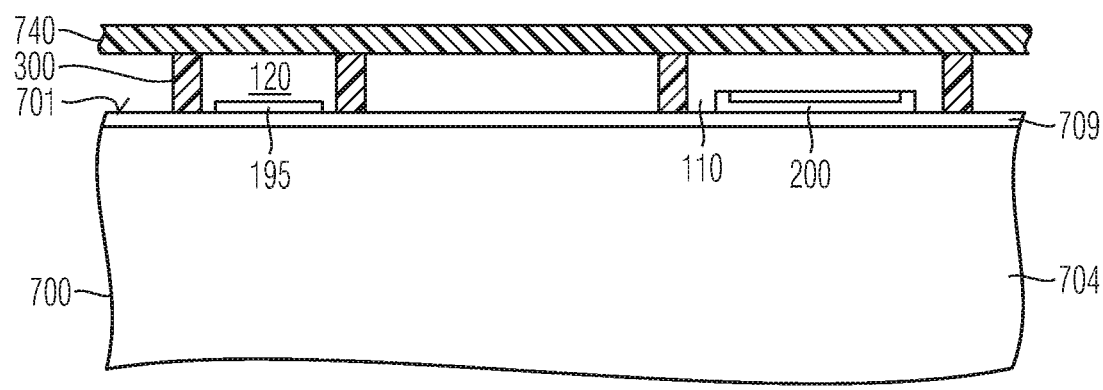
FIG. 11B is a schematic vertical cross-sectional view of the semiconductor substrate portion of FIG. 11A.

FIGS. 11A and 11B show the photoresist laminate 740 spanning across the frame structures 300 on the front surface 701 of the semiconductor substrate 700 thereby covering the first areas no laterally enclosed by the first loop portions 310, the second areas 120 laterally enclosed by the second loop portions 320 and the communicating channels 150 defined between parallel line sections 355 of the connection portion 350 of the frame structure 300. In case a sensitive surface 201 of the sensor unit 200 is on top of the sensor unit 200, i.e., opposite to the front surface 701, the photoresist laminate 740 is vertically spaced from the sensor unit 200 and the sensitive surface 201. The second photoresist material may be a negative photoresist that polymerizes under exposure. Portions of the photoresist laminate 740 are selectively exposed and developed.

Figure 12A:
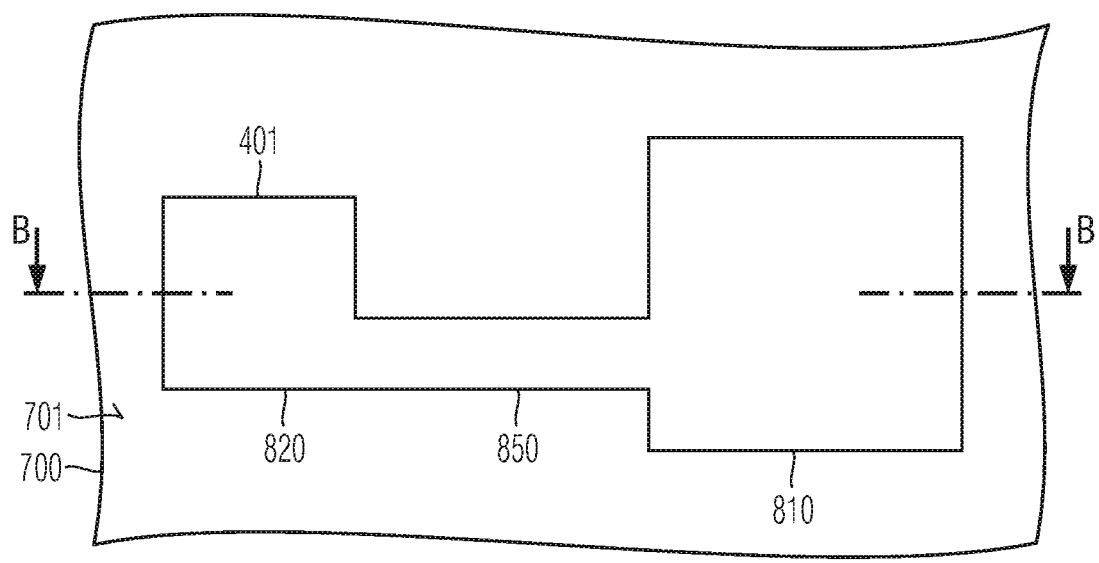
FIG. 12A is a schematic plan view of the semiconductor substrate portion of FIG. 11A, after forming a lid structure from the photoresist laminate.
Figure 12B:
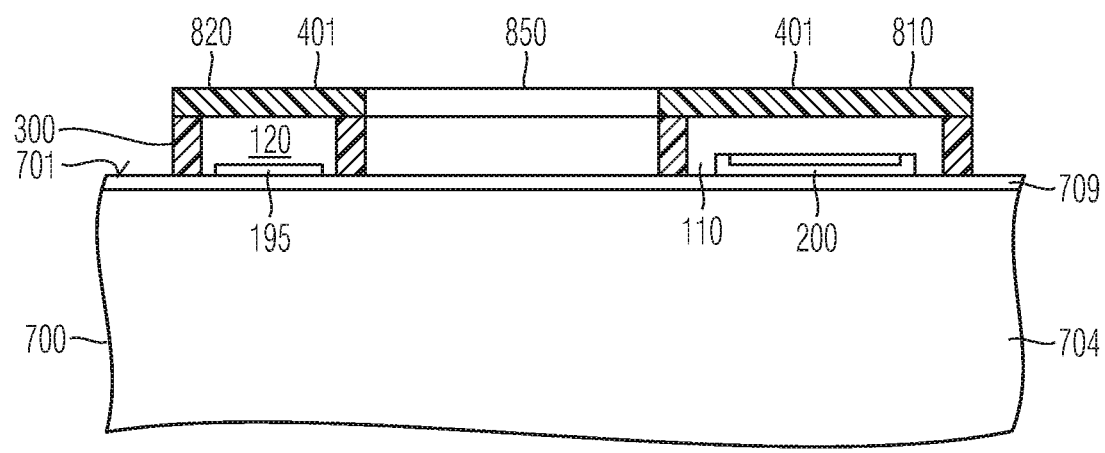
FIG. 12B is a schematic vertical cross-sectional view of the semiconductor substrate portion of FIG. 12A.

FIGS. 12A and 12B show a preparatory lid structure 401 formed from exposed portions of the photoresist laminate 740. The preparatory lid structure 401 completely covers the first area 110, the second area 120 and the communicating channel 150 such that during developing the interior of a sensor box 810 encasing the first area 110, an inlet box 820 encasing the second area 120 and a conduit 850 encasing the communicating channel 150 are hermetically closed and no developer material finds access to the interior of the sensor box 810, the conduit 850 and the inlet box 820.

A lid opening 490 is then formed in a section of the preparatory lid structure 401 above the second area 120 by irradiation with a laser beam to form the final lid structure 400. The laser may be, for example, an UV (ultraviolet) laser or a carbon-oxide laser. After exposing the second area 120, the laser beam impinges onto the reflective structure 195 that reflects the laser beam and in this way avoids a contamination of the communicating channel 150 with material the laser otherwise may ablate from the passivation layer 709.

Figure 13A:
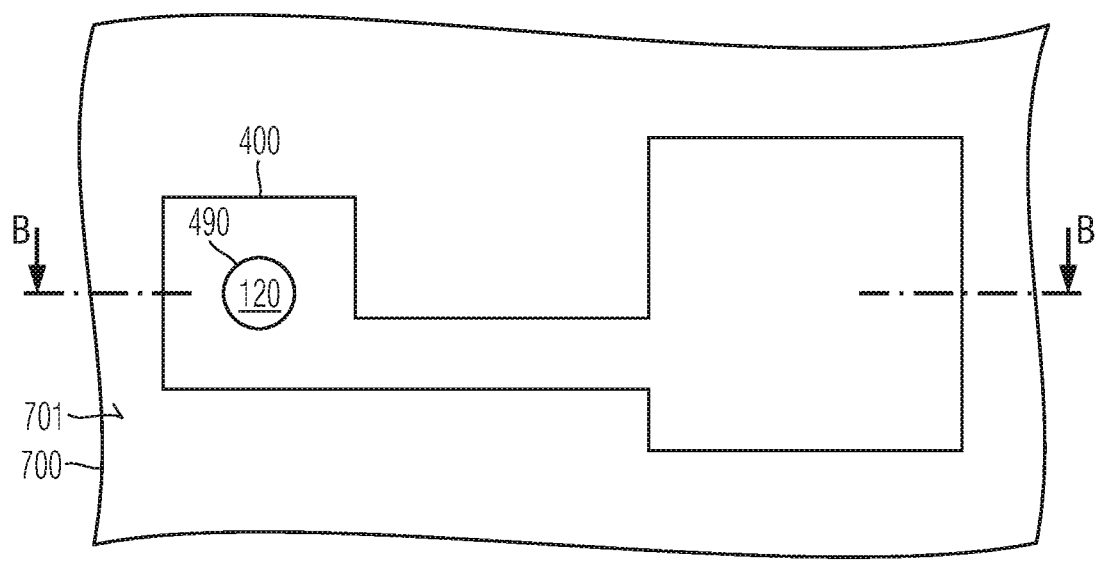
FIG. 13A is a schematic plan view of the semiconductor substrate portion of FIG. 12A, after forming a lid opening in the lid structure.
Figure 13B:
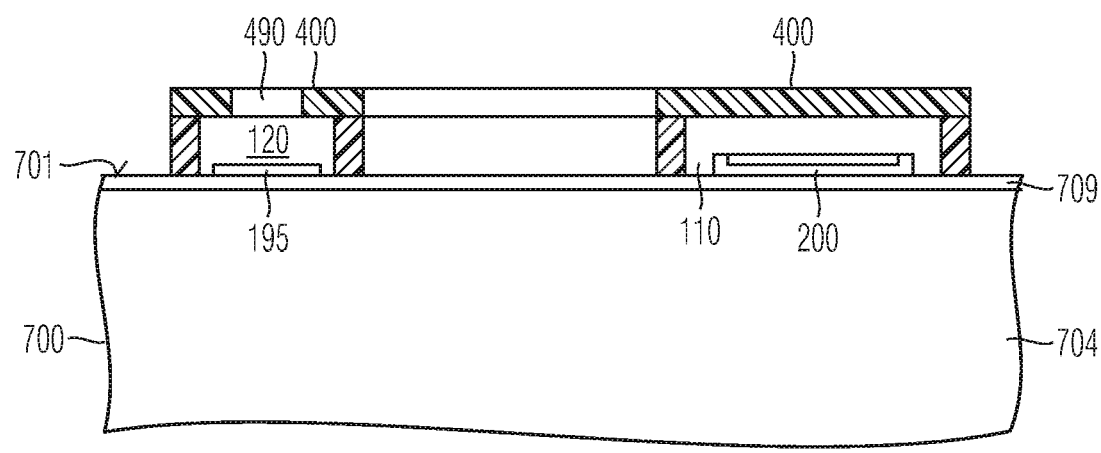
FIG. 13B is a schematic vertical cross-sectional view of the semiconductor substrate portion of FIG. 13A.

FIGS. 13A and 13B show the lid opening 490 in the vertical projection of the reflective structure 195. All processes concerning the formation of the frame structure 300 and the lid structure 400 are processes common in the BEOL processing of semiconductor wafers such that both the frame structure 300 and the lid structure 400 can be economically formed on wafer level.

Before or after forming the lid opening 490 but after forming the lid structure 400, a dicing process separates a plurality of identical sensor dies from the semiconductor substrate 700. The singularized sensor dies are then subjected to a packaging process that connects the contact pads of the single semiconductor dies to conductive packaging leads, for example, by wire bonding and that encapsulates the semiconductor dies in a mold compound 500 by a mold process using mold halves. The mold compound 500 is from a plastic that may contain non-plastic additives.

An upper mold half may have a protrusion pressed upon the top of the inlet box 820 around the lid opening 490 during molding. The liquid molding material is introduced into the closed mold and cured.

Figure 14A:
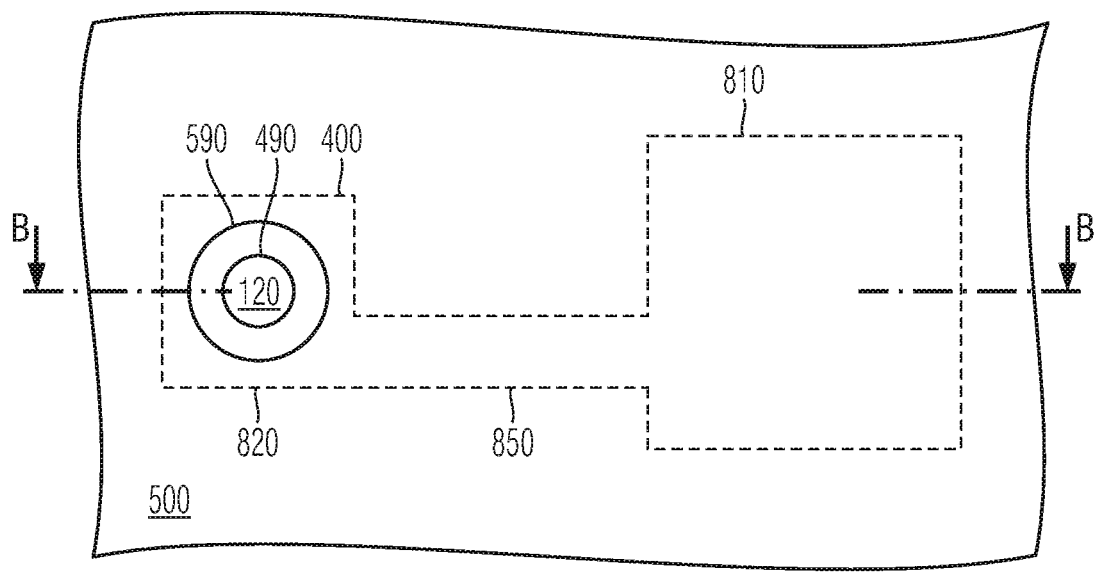
FIG. 14A is a schematic plan view of the semiconductor substrate portion of FIG. 13A, after forming a mold compound with a mold opening in the vertical projection of the lid opening.
Figure 14B:
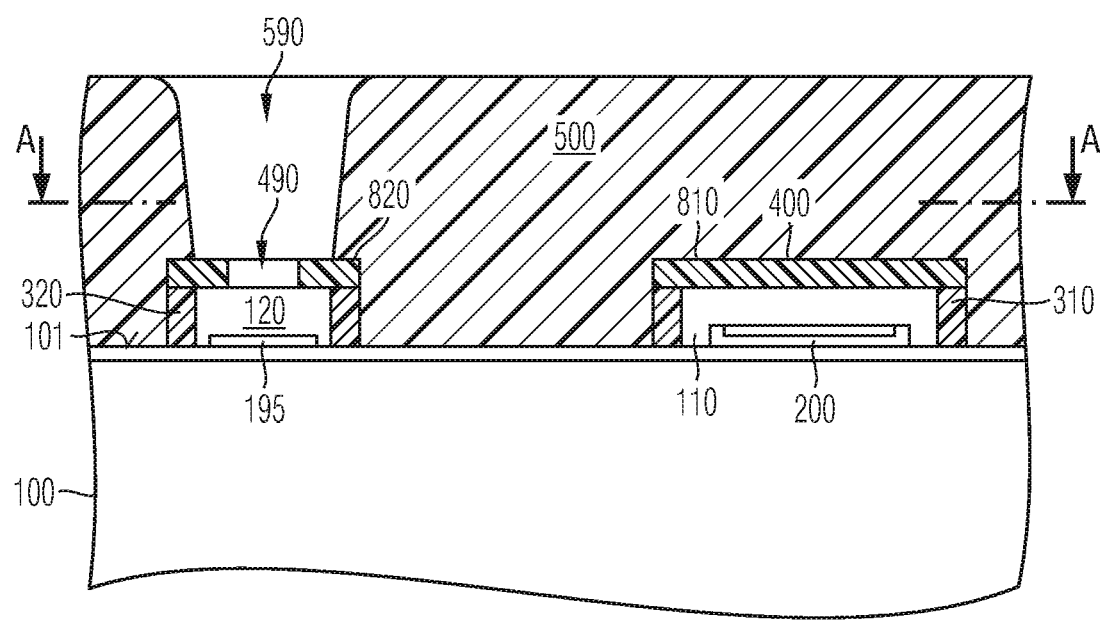
FIG. 14B is a schematic vertical cross-sectional view of the semiconductor substrate portion of FIG. 14A.

FIGS. 14A and 14B show the mold compound 500 embedding the sensor box 810, the conduit 850 and the inlet box 820, wherein a mold opening 590 exposes the lid opening 490.

FIGS. 15A to 19B refer to another embodiment for forming a lid opening by using a two-stage exposure process for the first photoresist material.

Starting from a semiconductor substrate 700 and a photoresist layer 730 as described in FIGS. 9A to 9B, a first exposure may polymerize the first photoresist material in the photoresist layer 730 in first portions corresponding to the final frame structure 300.

Figure 15A:
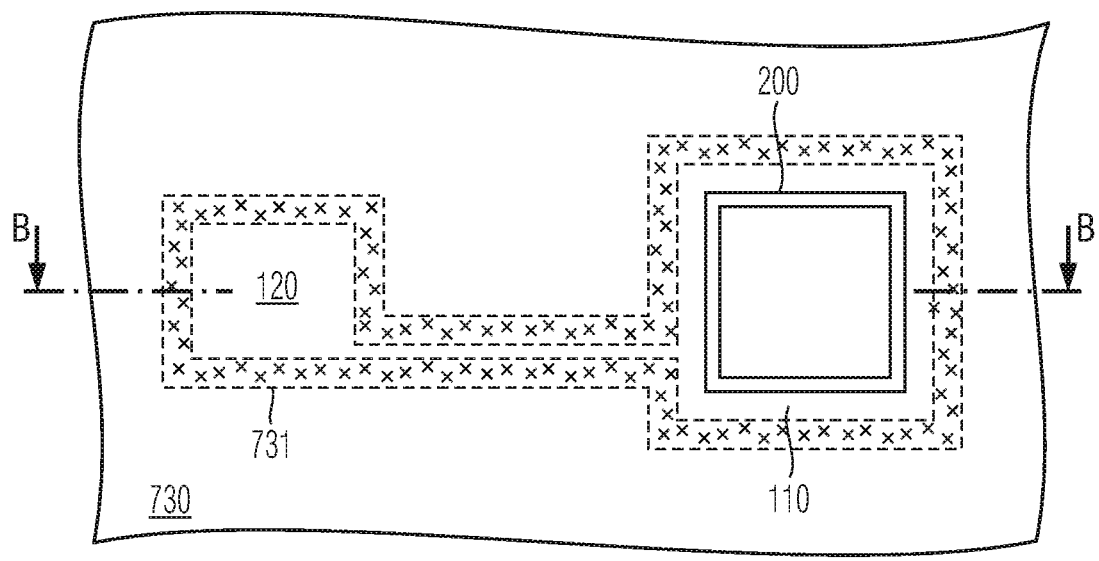
FIG. 15A is a schematic plan view of a portion of a semiconductor substrate for illustrating a method of manufacturing integrated sensor devices according to an embodiment forming a lid opening by using a double exposure of a photoresist layer, after a first exposure of the photoresist layer.
Figure 15B:
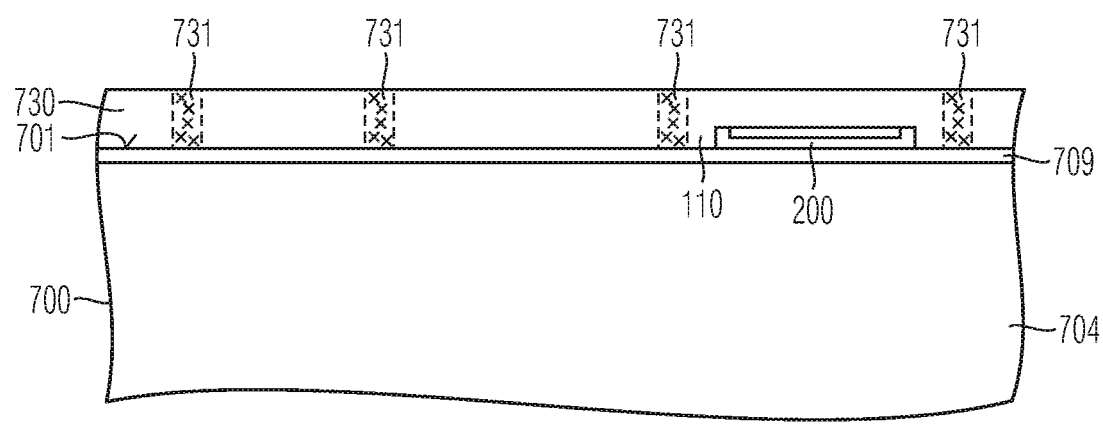
FIG. 15B is a schematic vertical cross-sectional view of the semiconductor substrate portion of FIG. 15A.

FIGS. 15A and 15B show the first polymerized sections 731 in the photoresist layer 730 after the first exposure. The first exposure polymerizes the first photoresist material in the complete vertical extension of the photoresist layer 730 from the surface of the photoresist layer 730 down to the front surface 701.

A second exposure of the first photoresist material selectively exposes a second portion of the photoresist layer 730 enclosed by the second loop portion 320 of the frame structure 300. In addition, the second exposure is carried out such that only a surface section of the photoresist layer 730 polymerizes in the exposed portion. For example, exposure time, exposure dose or exposure wavelength may be selected accordingly. According to an embodiment the transparency of the first photoresist material at the exposure wavelength of the second exposure may be lower than at the exposure wavelength of the first exposure such that the penetration depth of the exposure beam is smaller.

Figure 16A:
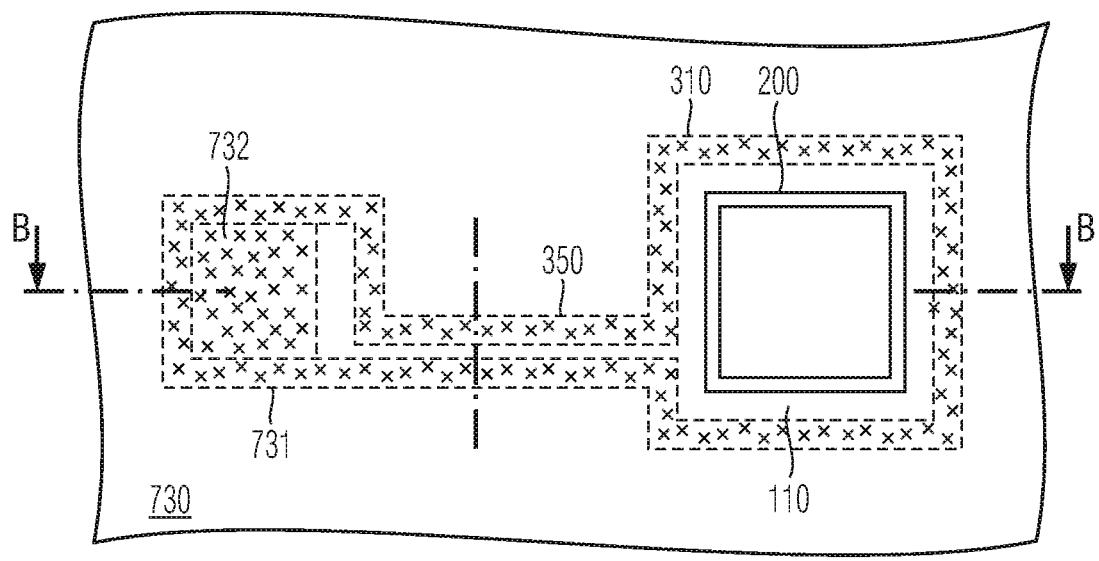
FIG. 16A is a schematic plan view of the semiconductor substrate portion of FIG. 15A, after a second exposure of the photoresist layer.
Figure 16B:
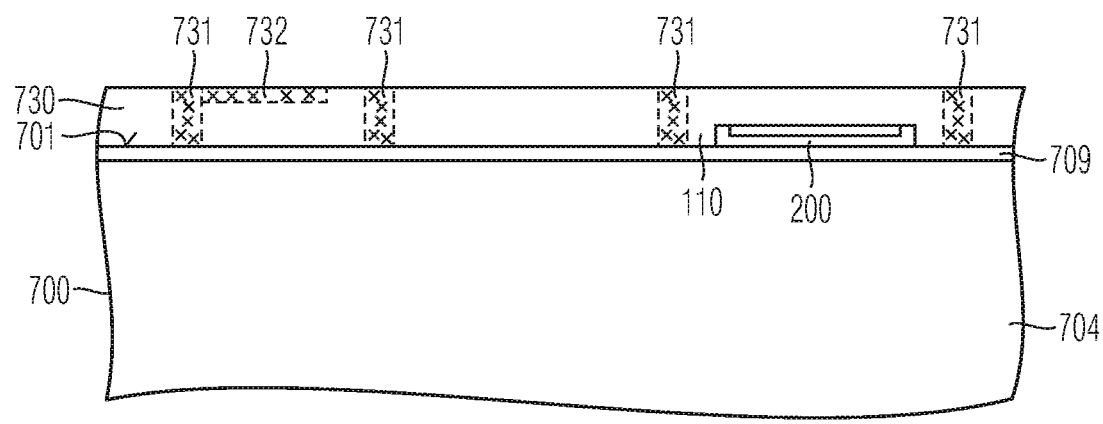
FIG. 16B is a schematic vertical cross-sectional view of the semiconductor substrate portion of FIG. 16A.

FIGS. 16A and 16B show a second polymerized section 732 of the photoresist layer 730. A vertical extension of the second polymerized section 732 of the photoresist layer 730 is at least 1 µm and at most half of the layer thickness of the photoresist layer 730. The sequence of the first and second exposure of the first photoresist material may be altered.

The first photoresist material is developed, wherein the developer liquid selectively removes unpolymerized portions of the photoresist layer 730 with respect to the polymerized first and second polymerized sections 731, 732 of the photoresist layer 730.

Figure 17A:
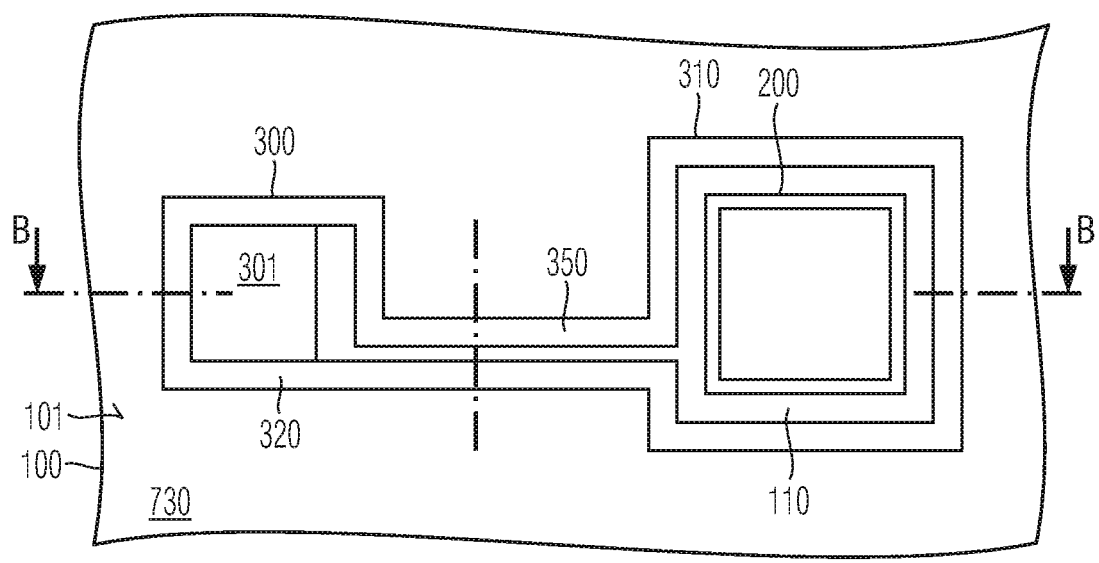
FIG. 17A is a schematic plan view of the semiconductor substrate portion of FIG. 16A, after developing the photoresist layer.
Figure 17B:
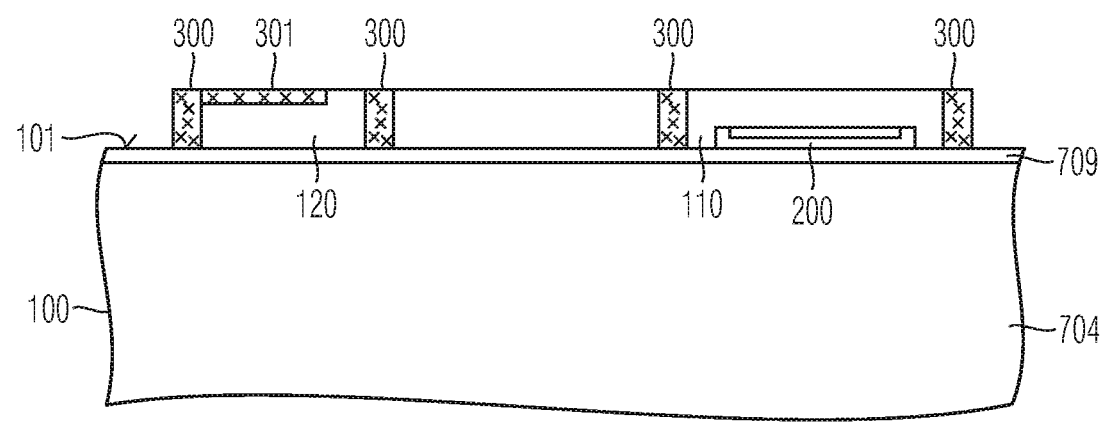
FIG. 17B is a schematic vertical cross-sectional view of the semiconductor substrate portion of FIG. 17A.

FIGS. 17A to 17B show the frame structure 300 resulting from the first polymerized section of the first photoresist material and an auxiliary lid 301 formed from the second polymerized section of the first photoresist material. The developer liquid undercuts the auxiliary lid 301 which is connected to the frame structure 300.

A photoresist laminate is attached on top of the frame structure 300. Other than in the previously described embodiment, an exposure of the photoresist laminate defines also the lid opening 490 in the lid structure 400, wherein the auxiliary lid 301 blocks the developer liquid from flowing into the inlet box 820, the conduit 850 and the sensor box 810.

Figure 18A:
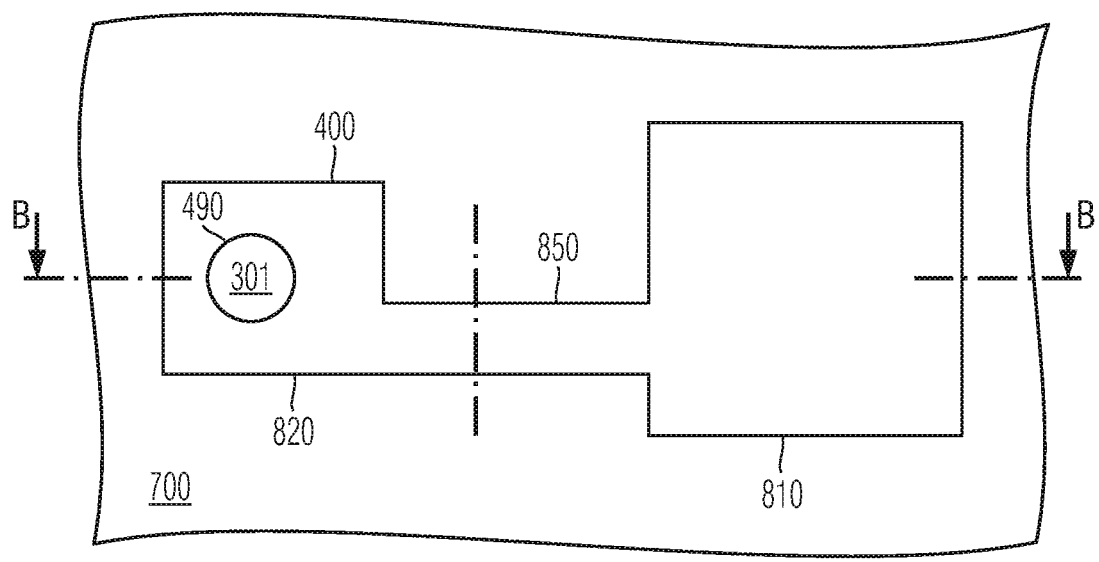
FIG. 18A is a schematic plan view of the semiconductor substrate portion of FIG. 17A, after developing a photoresist laminate disposed on the frame section.
Figure 18B:
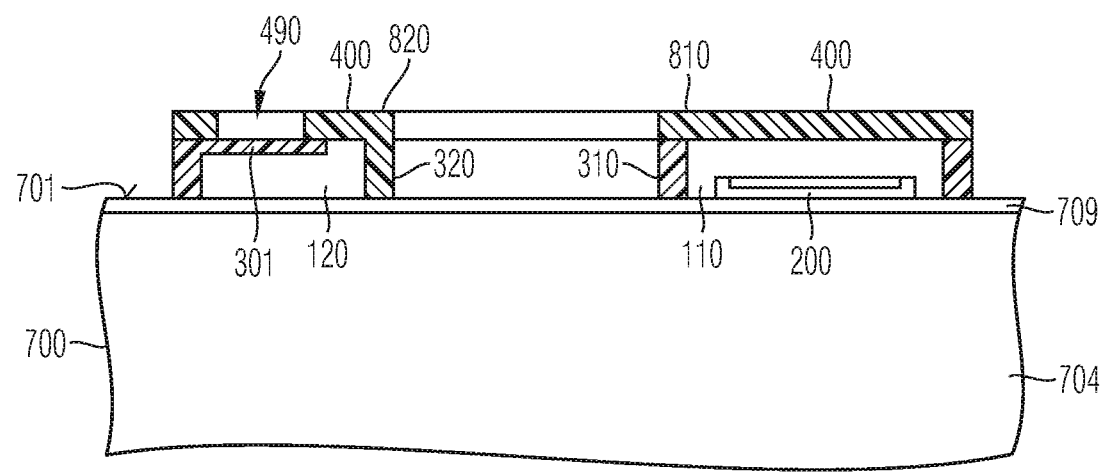
FIG. 18B is a schematic vertical cross-sectional view of the semiconductor substrate portion of FIG. 18A.

FIGS. 18A and 18B show the lid opening 490 that exposes the auxiliary lid 301. The exposed portion of the auxiliary lid 301 may be removed in a dry etch process that does hardly generate contaminants, for example, a plasma etch process in an atmosphere containing oxygen.

Figure 19A:
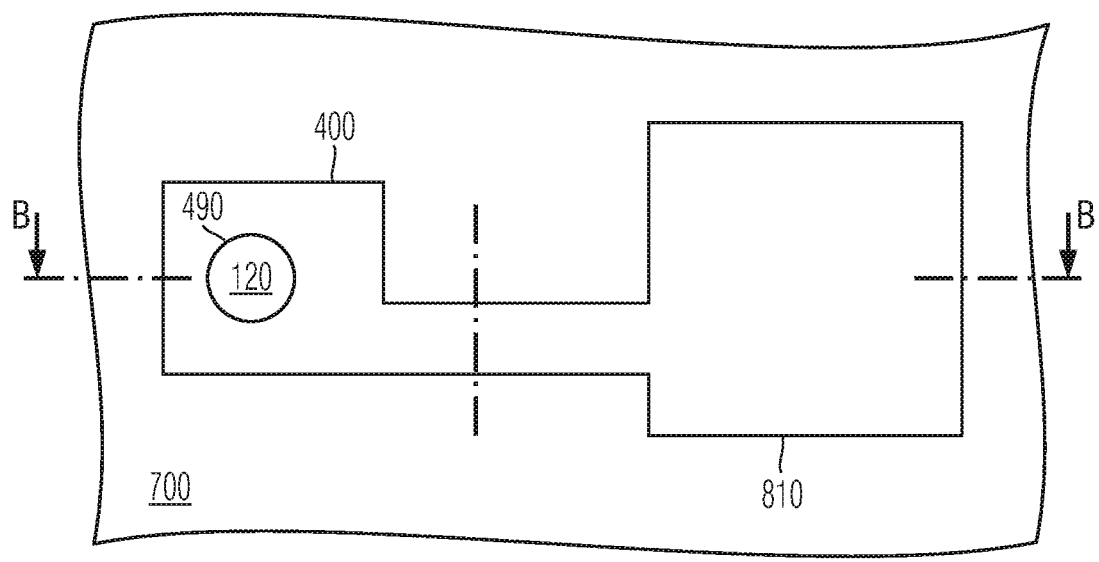
FIG. 19A is a schematic plan view of the semiconductor substrate portion of FIG. 18A, after opening an inlet box.
Figure 19B:
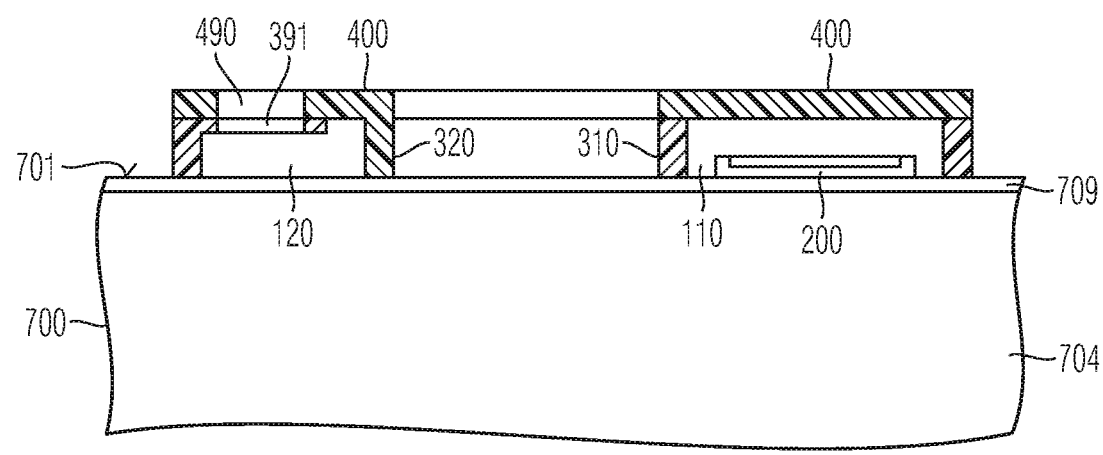
FIG. 19B is a schematic vertical cross-sectional view of the semiconductor substrate portion of FIG. 19A.

FIGS. 19A to 19B show the auxiliary lid opening 391 formed by the dry etch process in the vertical projection of the lid opening 490. Formation and opening of the auxiliary lid 301 gets along with standard BEOL processes and avoids a laser beam treatment. In addition, the method gets along without the reflective structure 195 of FIGS. 9A and 9B that may adversely affect other device characteristics, for example, a parasitic capacitance of conducting elements in the finalized sensor device.

Figure 20A:
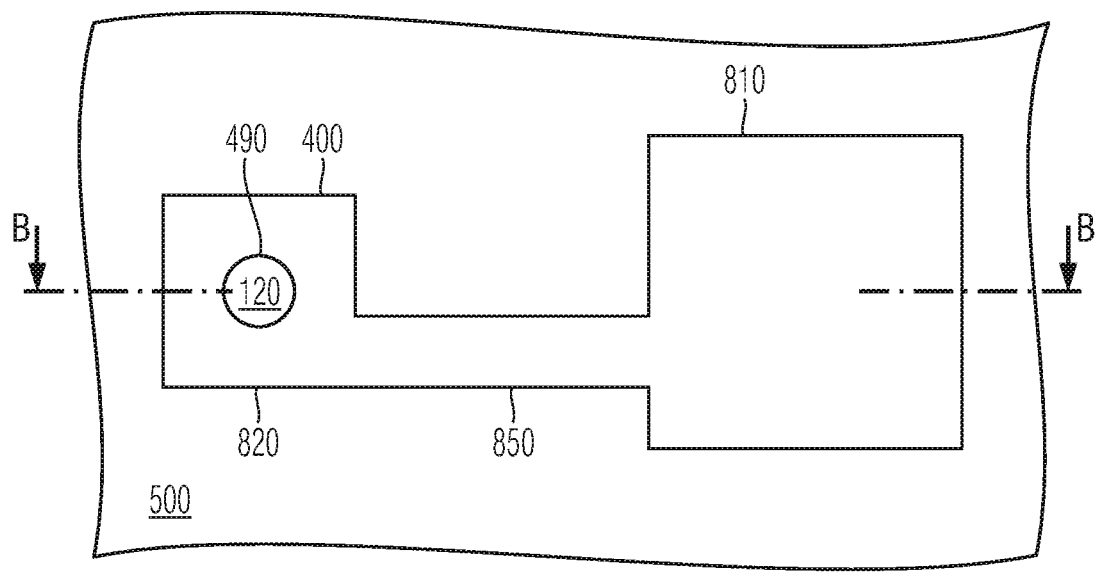
FIG. 20A is a schematic plan view of the semiconductor substrate portion of FIG. 14A, after grinding the mold compound according to a further embodiment.
Figure 20B:
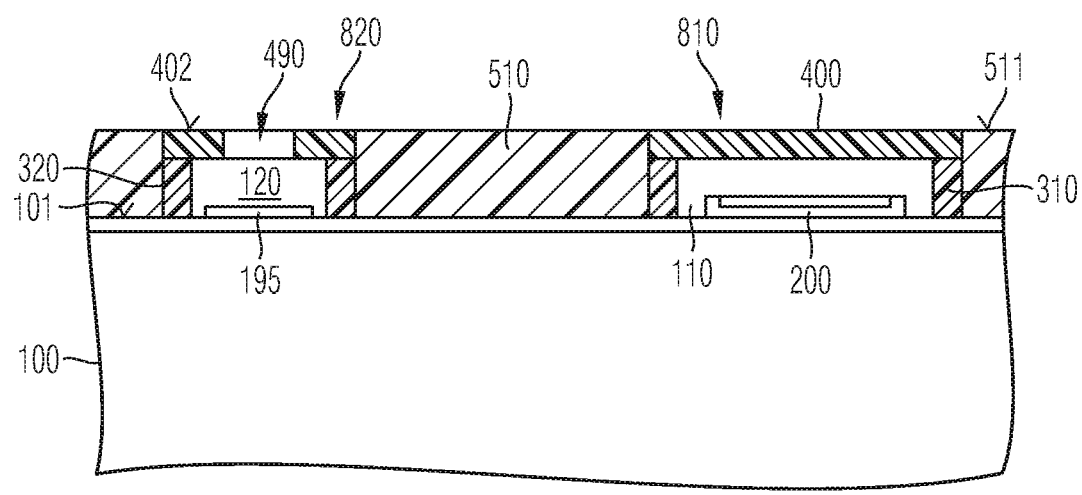
FIG. 20B is a schematic vertical cross-sectional view of the semiconductor substrate portion of FIG. 20A.

FIGS. 20A and 20B show a recessed mold compound 511 after an optional recess, e.g., a grinding or polishing of the mold compound 500 of FIGS. 14A to 14B down to a top surface 402 of the lid structure 400 such that the top surface 402 of the lid structure 400 and the top surface 511 of the recessed mold compound 511 are coplanar.

Although specific embodiments have been illustrated and described herein, it will be appreciated by those of ordinary skill in the art that a variety of alternate and/or equivalent implementations may be substituted for the specific embodiments shown and described without departing from the scope of the present invention. This application is intended to cover any adaptations or variations of the specific embodiments discussed herein. Therefore, it is intended that this invention be limited only by the claims and the equivalents thereof.

While this invention has been described with reference to illustrative embodiments, this description is not intended to be construed in a limiting sense. Various modifications and combinations of the illustrative embodiments, as well as other embodiments of the invention, will be apparent to persons skilled in the art upon reference to the description. It is therefore intended that the appended claims encompass any such modifications or embodiments.

What is claimed is:

1. A sensor device comprising:
    a sensor unit sensitive to a property of a gaseous medium, wherein the sensor unit is formed on a suspended mass mechanically connected to a sensor substrate through at least one spring bar;
    a frame structure on a first surface of the sensor substrate, wherein the frame structure comprises a first loop portion laterally surrounding a first area comprising the sensor unit;
    a communicating channel accessing the first area through a base port in the sensor substrate, wherein the base port comprises a spring groove separating the spring bar from one of the suspended mass and the sensor substrate; and
    a lid structure completely covering the frame structure and the first area.

2. The sensor device according to claim 1, wherein the lid structure is spaced from a sensitive surface of the sensor unit sensitive for the property of the gaseous medium.

3. The sensor device according to claim 1, wherein the frame structure comprises a developed first photoresist material.

4. The sensor device according to claim 1, wherein the lid structure comprises a developed second photoresist material.

5. The sensor device according to claim 1, wherein the communicating channel comprises a rear side cavity extending from a second surface opposite of the first surface into the sensor substrate and exposing the spring groove.

6. The sensor device according to claim 5, further comprising a carrier structure attached to the second surface, the carrier structure comprising an opening extending through the carrier structure and exposing the rear side cavity.

7. The sensor device according to claim 1, wherein the frame structure comprises a second loop portion on the first surface adjacent to the first loop portion, and the second loop portion surrounds a second area and the lid structure comprises a lid opening exposing the second area.

8. The sensor device according to claim 7, wherein:
the communicating channel comprises a substrate trench extending from a second surface opposite to the first surface into the sensor substrate, and
the communicating channel connects a wide portion of a rear side cavity in a vertical projection of the first area and a connection groove extending, in the second area, from the first surface into the sensor substrate.

9. The sensor device according to claim 8, further comprising a carrier structure attached to the second surface and closing the rear side cavity that extends from the second surface opposite of the first surface into the sensor substrate and that exposes the spring groove.

10. The sensor device according to claim 1, wherein the communicating channel comprises a substrate trench that comprises at least one rectangular bend.

11. The sensor device according to claim 10, wherein a vertical cross-sectional area of the substrate trench is uniform.

12. The sensor device according to claim 1, wherein the communicating channel comprises at least one narrow tube opening into at least one wide tube with a cross-sectional area at least twice as large as a cross-sectional area of the narrow tube.

13. The sensor device according to claim 1, wherein the communicating channel comprises at least two parallel first and second tubes, the first and second tubes extending from the first area to a second area.

14. The sensor device according to claim 1, wherein the frame structure is formed from straight line sections of uniform width.

15. The sensor device of claim 1, wherein:
the sensor unit is formed on the first surface of the sensor substrate;
the frame structure further comprises a second loop portion surrounding a second area, and a connection portion connecting the first loop portion with the second loop portion to form the communicating channel between the first and second areas; and
the lid structure further comprises a lid opening selectively exposing the second area.

16. The sensor device according to claim 15, wherein the lid structure is spaced from a sensitive surface of the sensor unit sensitive for the property of the gaseous medium.

17. The sensor device according to claim 15, wherein the frame structure is formed from a developed first photoresist material.

18. The sensor device according to claim 15, wherein the lid structure is formed from a developed second photoresist material.

19. The sensor device according to claim 15, wherein the communicating channel comprises at least one rectangular bend.

20. The sensor device according to claim 15, wherein a vertical cross-sectional area of the communicating channel is uniform between a lateral port or a base port opening into the first area and a port opening into the second area.

21. The sensor device according to claim 15, wherein the communicating channel comprises at least one narrow tube opening into at least one wide tube with a cross-sectional area at least twice as large as a cross-sectional area of the narrow tube.

22. The sensor device according to claim 15, wherein the communicating channel comprises at least two parallel first and second tubes, the first and second tubes extending from the first area to the second area.

23. The sensor device according to claim 15, wherein the communicating channel comprises at least two parallel first and second tubes, the parallel first and second tubes extending from a first wide tube to a second wide tube.

24. The sensor device according to claim 15, wherein the frame structure is formed from straight line sections of uniform width.

* * * * *